(12) United States Patent
Greenhalgh et al.

(10) Patent No.: US 9,050,112 B2
(45) Date of Patent: Jun. 9, 2015

(54) TISSUE REMOVAL DEVICE AND METHOD

(75) Inventors: E. Skott Greenhalgh, Lower Gwynedd, PA (US); Robert A. Kiefer, Quakertown, PA (US); Greg Anderson, Moorestown, NJ (US)

(73) Assignee: Flexmedex, LLC, Perkasie, PA (US)

( * ) Notice: Subject to any disclaimer, the term of this patent is extended or adjusted under 35 U.S.C. 154(b) by 54 days.

(21) Appl. No.: 13/592,271

(22) Filed: Aug. 22, 2012

(65) Prior Publication Data

US 2013/0053852 A1    Feb. 28, 2013

Related U.S. Application Data

(60) Provisional application No. 61/526,630, filed on Aug. 23, 2011.

(51) Int. Cl.
*A61B 17/00* (2006.01)
*A61B 17/16* (2006.01)

(52) U.S. Cl.
CPC ......... *A61B 17/1659* (2013.01); *A61B 17/1671* (2013.01)

(58) Field of Classification Search
CPC ............. A61B 17/148; A61B 17/1604; A61B 17/1671; A61B 17/1659
USPC .................................................... 606/82–84
See application file for complete search history.

(56) References Cited

U.S. PATENT DOCUMENTS

| 646,119 | A | 3/1900 | Clamer et al. |
|---|---|---|---|
| 4,204,531 | A | 5/1980 | Aginsky |
| 4,569,338 | A | 2/1986 | Edwards |
| 4,636,217 | A | 1/1987 | Ogilvie et al. |
| 4,653,489 | A | 3/1987 | Tronzo |
| 4,716,839 | A | 1/1988 | Catena |
| 4,716,893 | A | 1/1988 | Fischer et al. |
| 4,725,264 | A | 2/1988 | Glassman |
| 4,733,665 | A | 3/1988 | Palmaz |
| 4,759,769 | A | 7/1988 | Hedman et al. |
| 4,763,644 | A | 8/1988 | Webb |
| 4,863,476 | A | 9/1989 | Shepperd |
| 4,886,062 | A | 12/1989 | Wiktor |
| 4,911,718 | A | 3/1990 | Lee et al. |
| 4,932,975 | A | 6/1990 | Main et al. |
| 4,941,466 | A | 7/1990 | Romano |

(Continued)

FOREIGN PATENT DOCUMENTS

| EP | 0734702 | 10/1996 |
|---|---|---|
| EP | 0758541 | 2/1997 |

(Continued)

OTHER PUBLICATIONS

Franklin, I.J. et al., "Uptake of Tetracycline by Aortic Aneurysm Wall and Its Effect on Inflammation and Proteeolysis," *Brit. J. Surger*, 86(6):771-775, 1999.

(Continued)

*Primary Examiner* — Andrew Yang
(74) *Attorney, Agent, or Firm* — Levine Bagade Han LLP

(57) ABSTRACT

A tissue removal device for removing hard and/or soft tissue is disclosed. The device can have an elongated rigid shaft attached to an articulating broach. The device can be inserted through a transosseous delivery channel formed in a bone. The broach can articulate after passing through the transosseous delivery channel.

20 Claims, 10 Drawing Sheets

(56) References Cited

U.S. PATENT DOCUMENTS

| | | |
|---|---|---|
| 4,969,888 A | 11/1990 | Scholten et al. |
| 5,007,909 A | 4/1991 | Rogozinski |
| 5,015,247 A | 5/1991 | Michelson |
| 5,026,373 A | 6/1991 | Ray et al. |
| 5,059,193 A | 10/1991 | Kuslich |
| 5,108,404 A | 4/1992 | Scholten et al. |
| 5,123,926 A | 6/1992 | Pisharodi |
| 5,139,480 A | 8/1992 | Hickle et al. |
| 5,171,278 A | 12/1992 | Pisharodi |
| 5,217,483 A | 6/1993 | Tower |
| 5,258,031 A | 11/1993 | Salib et al. |
| 5,306,278 A | 4/1994 | Dahl et al. |
| 5,324,295 A | 6/1994 | Shapiro III |
| 5,342,348 A | 8/1994 | Kaplan |
| 5,345,927 A | 9/1994 | Bonutti |
| 5,390,683 A | 2/1995 | Pisharodi |
| 5,390,898 A | 2/1995 | Smedley et al. |
| 5,397,364 A | 3/1995 | Kozak et al. |
| 5,425,773 A | 6/1995 | Boyd et al. |
| 5,454,365 A | 10/1995 | Bonutti |
| 5,458,643 A | 10/1995 | Oka et al. |
| 5,480,442 A | 1/1996 | Bertagnoli |
| 5,484,384 A | 1/1996 | Fearnot |
| 5,496,365 A | 3/1996 | Sgro |
| 5,522,899 A | 6/1996 | Michelson |
| 5,534,002 A | 7/1996 | Brumfield et al. |
| 5,540,690 A | 7/1996 | Miller et al. |
| 5,549,679 A | 8/1996 | Kuslich |
| 5,554,191 A | 9/1996 | Lahille et al. |
| 5,556,413 A | 9/1996 | Lam |
| 5,562,736 A | 10/1996 | Ray et al. |
| 5,562,738 A | 10/1996 | Boyd et al. |
| 5,571,189 A | 11/1996 | Kuslich |
| 5,571,192 A | 11/1996 | Schonhoffer |
| 5,584,831 A | 12/1996 | McKay |
| 5,591,197 A | 1/1997 | Orth et al. |
| 5,593,409 A | 1/1997 | Michelson |
| 5,609,356 A | 3/1997 | Mossi |
| 5,609,635 A | 3/1997 | Michelson |
| 5,643,264 A | 7/1997 | Sherman et al. |
| 5,643,312 A | 7/1997 | Fischell et al. |
| 5,645,560 A | 7/1997 | Crocker et al. |
| 5,649,950 A | 7/1997 | Bourne et al. |
| 5,653,763 A | 8/1997 | Errico et al. |
| 5,658,335 A | 8/1997 | Allen |
| 5,665,122 A | 9/1997 | Kambin |
| 5,669,909 A | 9/1997 | Zdeblick et al. |
| 5,674,295 A | 10/1997 | Ray et al. |
| 5,683,394 A | 11/1997 | Rinner |
| 5,693,100 A | 12/1997 | Pisharodi |
| 5,702,449 A | 12/1997 | McKay |
| 5,702,453 A | 12/1997 | Rabbe et al. |
| 5,741,253 A | 4/1998 | Michelson |
| 5,749,916 A | 5/1998 | Richelsoph |
| 5,772,661 A | 6/1998 | Michelson |
| 5,776,181 A | 7/1998 | Lee et al. |
| 5,776,197 A | 7/1998 | Rabbe et al. |
| 5,776,198 A | 7/1998 | Rabbe et al. |
| 5,776,199 A | 7/1998 | Michelson |
| 5,782,832 A | 7/1998 | Larsen et al. |
| 5,782,903 A | 7/1998 | Wiktor |
| 5,785,710 A | 7/1998 | Michelson |
| 5,800,520 A | 9/1998 | Fogarty et al. |
| 5,824,054 A | 10/1998 | Khosravi et al. |
| 5,824,093 A | 10/1998 | Ray et al. |
| 5,827,289 A | 10/1998 | Reiley et al. |
| 5,827,321 A | 10/1998 | Roubin et al. |
| 5,853,419 A | 12/1998 | Imran |
| 5,861,025 A | 1/1999 | Boudghene et al. |
| 5,863,284 A | 1/1999 | Klein |
| 5,865,848 A | 2/1999 | Baker |
| 5,972,015 A | 10/1999 | Scribner et al. |
| 5,980,522 A | 11/1999 | Koros et al. |
| 5,980,550 A | 11/1999 | Eder et al. |
| 5,984,957 A | 11/1999 | Laptewicz et al. |
| 6,001,130 A | 12/1999 | Bryan et al. |
| 6,019,765 A | 2/2000 | Thornhill et al. |
| 6,019,792 A | 2/2000 | Cauthen |
| 6,022,376 A | 2/2000 | Assell et al. |
| 6,025,104 A | 2/2000 | Fuller et al. |
| 6,027,527 A | 2/2000 | Asano et al. |
| 6,036,719 A | 3/2000 | Meilus |
| 6,039,761 A | 3/2000 | Li et al. |
| 6,045,579 A | 4/2000 | Hochshuler et al. |
| 6,053,916 A | 4/2000 | Moore |
| 6,066,154 A | 5/2000 | Reiley et al. |
| 6,077,246 A | 6/2000 | Kullas et al. |
| 6,080,193 A | 6/2000 | Hochshuler et al. |
| 6,083,522 A | 7/2000 | Chu et al. |
| 6,086,610 A | 7/2000 | Duerig et al. |
| 6,090,143 A | 7/2000 | Meriwether et al. |
| 6,102,950 A | 8/2000 | Vaccaro |
| 6,113,639 A | 9/2000 | Ray et al. |
| 6,126,689 A | 10/2000 | Brett |
| 6,127,597 A | 10/2000 | Beyar et al. |
| 6,129,763 A | 10/2000 | Chauvin et al. |
| 6,132,465 A | 10/2000 | Ray et al. |
| 6,140,452 A | 10/2000 | Felt et al. |
| 6,146,417 A | 11/2000 | Ischinger |
| 6,159,244 A | 12/2000 | Suddaby |
| 6,159,245 A | 12/2000 | Meriwether et al. |
| 6,168,616 B1 | 1/2001 | Brown, III |
| 6,171,312 B1 | 1/2001 | Beaty |
| 6,176,882 B1 | 1/2001 | Biedermann et al. |
| 6,179,874 B1 | 1/2001 | Cauthen |
| 6,183,506 B1 | 2/2001 | Penn et al. |
| 6,183,517 B1 | 2/2001 | Suddaby |
| 6,193,757 B1 | 2/2001 | Foley et al. |
| 6,206,910 B1 | 3/2001 | Berry et al. |
| 6,206,924 B1 | 3/2001 | Timm |
| 6,224,595 B1 | 5/2001 | Michelson |
| 6,224,603 B1 | 5/2001 | Marino |
| 6,224,604 B1 | 5/2001 | Suddaby |
| 6,224,607 B1 | 5/2001 | Michelson |
| 6,235,043 B1 | 5/2001 | Reiley et al. |
| 6,241,734 B1 | 6/2001 | Scribner et al. |
| 6,245,101 B1 | 6/2001 | Drasler et al. |
| 6,245,107 B1 | 6/2001 | Ferree |
| 6,248,110 B1 | 6/2001 | Reiley et al. |
| 6,280,456 B1 | 8/2001 | Scribner et al. |
| 6,287,332 B1 | 9/2001 | Bolz et al. |
| 6,293,967 B1 | 9/2001 | Shanley |
| 6,302,914 B1 | 10/2001 | Michelson |
| 6,332,895 B1 | 12/2001 | Suddaby |
| 6,371,989 B1 | 4/2002 | Chauvin et al. |
| 6,387,130 B1 | 5/2002 | Stone et al. |
| 6,395,031 B1 | 5/2002 | Foley et al. |
| 6,402,750 B1 | 6/2002 | Atkinson et al. |
| 6,402,785 B1 | 6/2002 | Zdeblick et al. |
| 6,409,765 B1 | 6/2002 | Bianchi et al. |
| 6,419,704 B1 | 7/2002 | Ferree |
| 6,419,705 B1 | 7/2002 | Erickson |
| 6,423,083 B2 | 7/2002 | Reiley et al. |
| 6,425,916 B1 | 7/2002 | Garrison et al. |
| 6,425,919 B1 | 7/2002 | Lambrecht |
| 6,428,569 B1 | 8/2002 | Brown |
| 6,432,107 B1 | 8/2002 | Ferree |
| 6,436,098 B1 | 8/2002 | Michelson |
| 6,436,140 B1 | 8/2002 | Liu et al. |
| 6,440,168 B1 | 8/2002 | Cauthen |
| 6,447,544 B1 | 9/2002 | Michelson |
| 6,447,546 B1 | 9/2002 | Bramlet et al. |
| 6,447,547 B1 | 9/2002 | Michelson |
| 6,451,025 B1 | 9/2002 | Jervis |
| 6,454,804 B1 | 9/2002 | Ferree |
| 6,468,301 B1 | 10/2002 | Amplatz et al. |
| 6,468,302 B2 | 10/2002 | CoC et al. |
| 6,478,823 B1 | 11/2002 | Michelson |
| 6,482,235 B1 | 11/2002 | Lambrecht et al. |
| 6,488,710 B2 | 12/2002 | Besselink |
| 6,491,724 B1 | 12/2002 | Ferree |
| 6,494,883 B1 | 12/2002 | Ferree |
| 6,508,820 B2 | 1/2003 | Bales |
| 6,508,839 B1 | 1/2003 | Lambrecht et al. |

(56) References Cited

U.S. PATENT DOCUMENTS

| | | | |
|---|---|---|---|
| 6,514,255 B1 | 2/2003 | Ferree |
| 6,520,991 B2 | 2/2003 | Huene |
| 6,533,817 B1 | 3/2003 | Norton et al. |
| 6,554,833 B2 | 4/2003 | Levy et al. |
| 6,562,074 B2 | 5/2003 | Gerbec et al. |
| 6,582,431 B1 | 6/2003 | Ray |
| 6,582,467 B1 | 6/2003 | Teitelbaum et al. |
| 6,585,770 B1 | 7/2003 | White et al. |
| 6,592,589 B2 | 7/2003 | Hajianpour |
| 6,592,625 B2 | 7/2003 | Cauthen |
| 6,595,998 B2 | 7/2003 | Johnson et al. |
| 6,602,291 B1 | 8/2003 | Ray et al. |
| 6,607,530 B1 | 8/2003 | Carl et al. |
| 6,607,544 B1 | 8/2003 | Boucher et al. |
| 6,613,054 B2 | 9/2003 | Scribner et al. |
| 6,623,505 B2 | 9/2003 | Scribner et al. |
| 6,641,587 B2 | 11/2003 | Scribner et al. |
| 6,641,614 B1 | 11/2003 | Wagner et al. |
| 6,645,213 B2 | 11/2003 | Sand et al. |
| 6,645,247 B2 | 11/2003 | Ferree |
| 6,648,917 B2 | 11/2003 | Gerbec et al. |
| 6,648,918 B2 | 11/2003 | Ferree |
| 6,648,920 B2 | 11/2003 | Ferree |
| 6,652,584 B2 | 11/2003 | Michelson |
| 6,656,178 B1 | 12/2003 | Veldhuizen et al. |
| 6,663,647 B2 | 12/2003 | Reiley et al. |
| 6,666,891 B2 | 12/2003 | Boehm, Jr. et al. |
| 6,676,665 B2 | 1/2004 | Foley et al. |
| 6,679,915 B1 | 1/2004 | Cauthen |
| 6,685,695 B2 | 2/2004 | Ferree |
| 6,695,760 B1 | 2/2004 | Winkler et al. |
| 6,706,068 B2 | 3/2004 | Ferree |
| 6,706,070 B1 | 3/2004 | Wagner et al. |
| 6,709,458 B2 | 3/2004 | Michelson |
| 6,712,853 B2 | 3/2004 | Kuslich |
| 6,716,216 B1 | 4/2004 | Boucher et al. |
| 6,716,247 B2 | 4/2004 | Michelson |
| 6,719,773 B1 | 4/2004 | Boucher et al. |
| 6,723,126 B1 | 4/2004 | Berry |
| 6,726,691 B2 | 4/2004 | Osorio et al. |
| 6,733,535 B2 | 5/2004 | Michelson |
| 6,740,090 B1 | 5/2004 | Cragg et al. |
| 6,743,255 B2 | 6/2004 | Ferree |
| 6,746,451 B2 | 6/2004 | Middleton et al. |
| 6,758,863 B2 | 7/2004 | Estes et al. |
| 6,793,656 B1 | 9/2004 | Mathews |
| 6,793,679 B2 | 9/2004 | Michelson |
| 6,808,537 B2 | 10/2004 | Michelson |
| 6,814,756 B1 | 11/2004 | Michelson |
| 6,830,589 B2 | 12/2004 | Erickson |
| 6,852,115 B2 | 2/2005 | Kinnett |
| 6,852,123 B2 | 2/2005 | Brown |
| 6,852,129 B2 | 2/2005 | Gerbec et al. |
| 6,863,673 B2 | 3/2005 | Gerbec et al. |
| 6,893,464 B2 | 5/2005 | Kiester |
| 6,899,716 B2 | 5/2005 | Cragg |
| 6,899,719 B2 | 5/2005 | Reiley et al. |
| 6,921,264 B2 | 7/2005 | Mayer et al. |
| 6,923,813 B2 | 8/2005 | Phillips et al. |
| 6,923,830 B2 | 8/2005 | Michelson |
| 6,936,065 B2 | 8/2005 | Khan et al. |
| 6,936,070 B1 | 8/2005 | Muhanna |
| 6,948,223 B2 | 9/2005 | Shortt |
| 6,953,477 B2 | 10/2005 | Berry |
| 6,955,691 B2 | 10/2005 | Chae et al. |
| 6,960,215 B2 | 11/2005 | Olson et al. |
| 6,962,606 B2 | 11/2005 | Michelson |
| 6,981,981 B2 | 1/2006 | Reiley et al. |
| 7,008,453 B1 | 3/2006 | Michelson |
| 7,018,415 B1 | 3/2006 | McKay |
| 7,018,416 B2 | 3/2006 | Hanson et al. |
| 7,056,321 B2 | 6/2006 | Pagliuca et al. |
| 7,066,961 B2 | 6/2006 | Michelson |
| 7,077,864 B2 | 7/2006 | Byrd et al. |
| 7,087,055 B2 | 8/2006 | Lim et al. |
| 7,094,257 B2 | 8/2006 | Mujwid et al. |
| 7,097,648 B1 | 8/2006 | Globerman et al. |
| 7,112,206 B2 | 9/2006 | Michelson |
| 7,118,598 B2 | 10/2006 | Michelson |
| 7,135,043 B2 | 11/2006 | Nakahara et al. |
| 7,166,110 B2 | 1/2007 | Yundt |
| 7,201,751 B2 | 4/2007 | Zucherman et al. |
| 7,201,775 B2 | 4/2007 | Gorensek et al. |
| 7,204,853 B2 | 4/2007 | Gordon et al. |
| 7,211,112 B2 | 5/2007 | Baynham et |
| 7,212,480 B2 | 5/2007 | Shoji et al. |
| 7,223,292 B2 | 5/2007 | Messerli et al. |
| 7,226,475 B2 | 6/2007 | Lenz et al. |
| 7,226,481 B2 | 6/2007 | Kuslich |
| 7,226,483 B2 | 6/2007 | Gerber et al. |
| 7,238,186 B2 | 7/2007 | Zdeblick et al. |
| 7,241,297 B2 | 7/2007 | Shaolian et al. |
| 7,241,303 B2 | 7/2007 | Reiss et al. |
| 7,300,440 B2 | 11/2007 | Zdeblick et al. |
| 7,309,338 B2 | 12/2007 | Cragg |
| 7,311,713 B2 | 12/2007 | Johnson et al. |
| 7,316,714 B2 | 1/2008 | Gordon et al. |
| 7,318,826 B2 | 1/2008 | Teitelbaum et al. |
| 7,396,360 B2 | 7/2008 | Lieberman |
| 7,431,735 B2 | 10/2008 | Liu et al. |
| 7,452,371 B2 | 11/2008 | Pavcnik et al. |
| 7,503,933 B2 | 3/2009 | Michelson |
| 7,507,241 B2 | 3/2009 | Levy et al. |
| 7,582,106 B2 | 9/2009 | Teitelbaum et al. |
| 7,601,172 B2 | 10/2009 | Segal et al. |
| 7,618,457 B2 | 11/2009 | Hudgins |
| 7,621,950 B1 | 11/2009 | Globerman et al. |
| 7,722,674 B1 | 5/2010 | Grotz |
| 7,749,228 B2 | 7/2010 | Lieberman |
| 7,763,028 B2 | 7/2010 | Lim et al. |
| 7,828,849 B2 | 11/2010 | Lim |
| 7,837,734 B2 | 11/2010 | Zucherman et al. |
| 7,867,233 B2 | 1/2011 | Shaolian et al. |
| 7,875,035 B2 | 1/2011 | Boucher et al. |
| 7,879,036 B2 | 2/2011 | Biedermann et al. |
| 7,879,082 B2 | 2/2011 | Brown |
| 7,960,073 B2 | 6/2011 | Park et al. |
| 8,007,498 B2 | 8/2011 | Mische |
| 8,034,110 B2 | 10/2011 | Garner et al. |
| 8,105,382 B2 | 1/2012 | Olmos et al. |
| 8,142,507 B2 | 3/2012 | McGuckin |
| 8,162,943 B2 | 4/2012 | Justin et al. |
| 8,206,423 B2 | 6/2012 | Siegal |
| 8,246,622 B2 * | 8/2012 | Siegal et al. .................. 606/80 |
| 8,465,524 B2 | 6/2013 | Siegal |
| 8,486,149 B2 | 7/2013 | Saidha et al. |
| 8,512,408 B2 | 8/2013 | Miller et al. |
| 8,551,171 B2 | 10/2013 | Johnson et al. |
| 8,591,582 B2 | 11/2013 | Anderson et al. |
| 8,672,968 B2 | 3/2014 | Stone et al. |
| 8,672,977 B2 | 3/2014 | Siegal et al. |
| 8,777,993 B2 | 7/2014 | Siegal et al. |
| 2001/0007956 A1 | 7/2001 | Letac et al. |
| 2001/0034552 A1 | 10/2001 | Young et al. |
| 2002/0007218 A1 | 1/2002 | Cauthen |
| 2002/0010511 A1 | 1/2002 | Michelson |
| 2002/0022887 A1 | 2/2002 | Huene |
| 2002/0032444 A1 | 3/2002 | Mische |
| 2002/0052656 A1 | 5/2002 | Michelson |
| 2002/0068911 A1 | 6/2002 | Chan |
| 2002/0068939 A1 | 6/2002 | Levy et al. |
| 2002/0068975 A1 | 6/2002 | Teitelbaum et al. |
| 2002/0068976 A1 | 6/2002 | Jackson |
| 2002/0068977 A1 | 6/2002 | Jackson |
| 2002/0082598 A1 | 6/2002 | Teitelbaum |
| 2002/0082600 A1 | 6/2002 | Shaolian et al. |
| 2002/0091390 A1 | 7/2002 | Michelson |
| 2002/0095155 A1 | 7/2002 | Michelson |
| 2002/0099378 A1 | 7/2002 | Michelson |
| 2002/0111688 A1 | 8/2002 | Cauthen |
| 2002/0120337 A1 | 8/2002 | Cauthen |
| 2002/0123807 A1 | 9/2002 | Cauthen |
| 2002/0128713 A1 | 9/2002 | Ferree |
| 2002/0138077 A1 | 9/2002 | Ferree |

(56) References Cited

U.S. PATENT DOCUMENTS

| | | |
|---|---|---|
| 2002/0138133 A1 | 9/2002 | Lenz et al. |
| 2002/0138144 A1 | 9/2002 | Michelson |
| 2002/0143401 A1 | 10/2002 | Michelson |
| 2002/0151896 A1 | 10/2002 | Ferree |
| 2002/0151980 A1 | 10/2002 | Cauthen |
| 2002/0156530 A1 | 10/2002 | Lambrecht et al. |
| 2002/0161367 A1 | 10/2002 | Ferree |
| 2002/0161373 A1 | 10/2002 | Osorio et al. |
| 2002/0165542 A1 | 11/2002 | Ferree |
| 2002/0189622 A1 | 12/2002 | Cauthen et al. |
| 2002/0198526 A1 | 12/2002 | Shaolian et al. |
| 2003/0004511 A1 | 1/2003 | Ferree |
| 2003/0004574 A1 | 1/2003 | Ferree |
| 2003/0009227 A1 | 1/2003 | Lambrecht et al. |
| 2003/0014118 A1 | 1/2003 | Lambrecht et al. |
| 2003/0026788 A1 | 2/2003 | Ferree |
| 2003/0032963 A1 | 2/2003 | Reiss et al. |
| 2003/0040796 A1 | 2/2003 | Ferree |
| 2003/0040798 A1 | 2/2003 | Michelson |
| 2003/0050701 A1 | 3/2003 | Michelson |
| 2003/0065394 A1 | 4/2003 | Michelson |
| 2003/0065396 A1 | 4/2003 | Michelson |
| 2003/0074076 A1 | 4/2003 | Ferree et al. |
| 2003/0078579 A1 | 4/2003 | Ferree |
| 2003/0088249 A1 | 5/2003 | Furderer |
| 2003/0120345 A1 | 6/2003 | Cauthen |
| 2003/0125748 A1 | 7/2003 | Li et al. |
| 2003/0125807 A1 | 7/2003 | Lambrecht et al. |
| 2003/0135220 A1 | 7/2003 | Cauthen |
| 2003/0135279 A1 | 7/2003 | Michelson |
| 2003/0149482 A1 | 8/2003 | Michelson |
| 2003/0153976 A1 | 8/2003 | Cauthen et al. |
| 2003/0158553 A1 | 8/2003 | Michelson |
| 2003/0158604 A1 | 8/2003 | Cauthen et al. |
| 2003/0163200 A1 | 8/2003 | Cauthen |
| 2003/0181979 A1 | 9/2003 | Ferree |
| 2003/0181980 A1 | 9/2003 | Berry et al. |
| 2003/0181983 A1 | 9/2003 | Cauthen |
| 2003/0187507 A1 | 10/2003 | Cauthen |
| 2003/0187508 A1 | 10/2003 | Cauthen |
| 2003/0191536 A1 | 10/2003 | Ferree |
| 2003/0195514 A1 | 10/2003 | Trieu et al. |
| 2003/0195630 A1 | 10/2003 | Ferree |
| 2003/0195631 A1 | 10/2003 | Ferree |
| 2003/0199979 A1 | 10/2003 | McGuckin |
| 2003/0199981 A1 | 10/2003 | Ferree |
| 2003/0204260 A1 | 10/2003 | Ferree |
| 2003/0208270 A9 | 11/2003 | Michelson |
| 2003/0220643 A1 | 11/2003 | Ferree |
| 2003/0220650 A1 | 11/2003 | Major et al. |
| 2003/0220690 A1 | 11/2003 | Cauthen |
| 2003/0220693 A1 | 11/2003 | Cauthen |
| 2003/0220694 A1 | 11/2003 | Cauthen |
| 2003/0233097 A1 | 12/2003 | Ferree |
| 2003/0233148 A1 | 12/2003 | Ferree |
| 2003/0233188 A1 | 12/2003 | Jones |
| 2003/0236520 A1 | 12/2003 | Lim et al. |
| 2004/0002759 A1 | 1/2004 | Ferree |
| 2004/0002760 A1 | 1/2004 | Boyd et al. |
| 2004/0002769 A1 | 1/2004 | Ferree |
| 2004/0006341 A1 | 1/2004 | Shaolian et al. |
| 2004/0006344 A1 | 1/2004 | Nguyen et al. |
| 2004/0010315 A1 | 1/2004 | Song |
| 2004/0010318 A1 | 1/2004 | Ferree |
| 2004/0019386 A1 | 1/2004 | Ferree |
| 2004/0024400 A1 | 2/2004 | Michelson |
| 2004/0024459 A1 | 2/2004 | Ferree |
| 2004/0024460 A1 | 2/2004 | Ferree |
| 2004/0024461 A1 | 2/2004 | Ferree |
| 2004/0024462 A1 | 2/2004 | Ferree et al. |
| 2004/0024469 A1 | 2/2004 | Ferree |
| 2004/0024471 A1 | 2/2004 | Ferree |
| 2004/0028718 A1 | 2/2004 | Ferree |
| 2004/0030387 A1 | 2/2004 | Landry et al. |
| 2004/0030389 A1 | 2/2004 | Ferree |
| 2004/0030390 A1 | 2/2004 | Ferree |
| 2004/0030391 A1 | 2/2004 | Ferree |
| 2004/0030398 A1 | 2/2004 | Ferree |
| 2004/0034357 A1 | 2/2004 | Beane et al. |
| 2004/0044410 A1 | 3/2004 | Ferree et al. |
| 2004/0049289 A1 | 3/2004 | Tordy et al. |
| 2004/0059418 A1 | 3/2004 | McKay et al. |
| 2004/0059419 A1 | 3/2004 | Michelson |
| 2004/0059429 A1 | 3/2004 | Amin et al. |
| 2004/0068259 A1 | 4/2004 | Michelson |
| 2004/0082954 A1 | 4/2004 | Teitelbaum et al. |
| 2004/0082961 A1 | 4/2004 | Teitelbaum |
| 2004/0087950 A1 | 5/2004 | Teitelbaum |
| 2004/0092933 A1 | 5/2004 | Shaolian et al. |
| 2004/0092988 A1 | 5/2004 | Shaolian et al. |
| 2004/0097927 A1 | 5/2004 | Yeung et al. |
| 2004/0111108 A1 | 6/2004 | Farnan |
| 2004/0133229 A1 | 7/2004 | Lambrecht et al. |
| 2004/0133280 A1 | 7/2004 | Trieu |
| 2004/0138673 A1 | 7/2004 | Lambrecht et al. |
| 2004/0153064 A1 | 8/2004 | Foley et al. |
| 2004/0153065 A1 | 8/2004 | Lim |
| 2004/0153146 A1 | 8/2004 | Lashinski et al. |
| 2004/0167625 A1 | 8/2004 | Beyar et al. |
| 2005/0010292 A1 | 1/2005 | Carrasco |
| 2005/0015152 A1 | 1/2005 | Sweeney |
| 2005/0033431 A1 | 2/2005 | Gordon et al. |
| 2005/0038512 A1 | 2/2005 | Michelson |
| 2005/0043796 A1 | 2/2005 | Grant et al. |
| 2005/0070911 A1 | 3/2005 | Carrison et al. |
| 2005/0080422 A1 | 4/2005 | Otte et al. |
| 2005/0085910 A1 | 4/2005 | Sweeney |
| 2005/0107863 A1 | 5/2005 | Brown |
| 2005/0113919 A1 | 5/2005 | Cragg et al. |
| 2005/0113928 A1 | 5/2005 | Cragg et al. |
| 2005/0119561 A1 | 6/2005 | Kienzle |
| 2005/0143827 A1 | 6/2005 | Globerman et al. |
| 2005/0182463 A1 | 8/2005 | Hunter et al. |
| 2005/0187558 A1 | 8/2005 | Johnson et al. |
| 2005/0209698 A1 | 9/2005 | Gordon et al. |
| 2005/0228391 A1 | 10/2005 | Levy et al. |
| 2005/0240188 A1 | 10/2005 | Chow et al. |
| 2005/0249776 A1 | 11/2005 | Chen et al. |
| 2005/0261683 A1 | 11/2005 | Veldhuizen et al. |
| 2005/0261768 A1 | 11/2005 | Trieu |
| 2005/0261781 A1 | 11/2005 | Sennett et al. |
| 2005/0278023 A1 | 12/2005 | Zwirkoski |
| 2005/0278026 A1 | 12/2005 | Gordon et al. |
| 2005/0278036 A1 | 12/2005 | Leonard et al. |
| 2006/0004455 A1 | 1/2006 | Leonard et al. |
| 2006/0015184 A1 | 1/2006 | Winterbottom et al. |
| 2006/0036241 A1 | 2/2006 | Siegal |
| 2006/0036273 A1 | 2/2006 | Siegal |
| 2006/0052788 A1 | 3/2006 | Thelen et al. |
| 2006/0052870 A1 | 3/2006 | Ferree |
| 2006/0058807 A1 | 3/2006 | Landry et al. |
| 2006/0058876 A1 | 3/2006 | McKinley |
| 2006/0058880 A1 | 3/2006 | Wysocki et al. |
| 2006/0085069 A1 | 4/2006 | Kim |
| 2006/0085070 A1 | 4/2006 | Kim |
| 2006/0089715 A1 | 4/2006 | Truckai et al. |
| 2006/0100706 A1 | 5/2006 | Shadduck et al. |
| 2006/0106460 A1 | 5/2006 | Messerli et al. |
| 2006/0122701 A1 | 6/2006 | Kiester |
| 2006/0142858 A1 | 6/2006 | Colleran et al. |
| 2006/0142859 A1 | 6/2006 | McLuen |
| 2006/0149239 A1 | 7/2006 | Winslow et al. |
| 2006/0149349 A1 | 7/2006 | Garbe |
| 2006/0149385 A1 | 7/2006 | McKay |
| 2006/0155379 A1 | 7/2006 | Heneveld |
| 2006/0161261 A1 | 7/2006 | Brown et al. |
| 2006/0178694 A1 | 8/2006 | Greenhalgh et al. |
| 2006/0184188 A1 | 8/2006 | Li et al. |
| 2006/0189999 A1 | 8/2006 | Zwirkoski |
| 2006/0200166 A1 | 9/2006 | Hanson et al. |
| 2006/0206207 A1 | 9/2006 | Dryer et al. |
| 2006/0235423 A1 | 10/2006 | Cantu |
| 2006/0241764 A1 | 10/2006 | Michelson |
| 2006/0253201 A1 | 11/2006 | McLuen |

(56) References Cited

U.S. PATENT DOCUMENTS

| | | |
|---|---|---|
| 2006/0264968 A1 | 11/2006 | Frey et al. |
| 2006/0271061 A1 | 11/2006 | Beyar et al. |
| 2006/0287725 A1 | 12/2006 | Miller |
| 2006/0287726 A1 | 12/2006 | Segal et al. |
| 2006/0287727 A1 | 12/2006 | Segal et al. |
| 2006/0287729 A1 | 12/2006 | Segal et al. |
| 2006/0287730 A1 | 12/2006 | Segal et al. |
| 2007/0027363 A1 | 2/2007 | Gannoe et al. |
| 2007/0032791 A1 | 2/2007 | Greenhalgh |
| 2007/0043440 A1 | 2/2007 | William et al. |
| 2007/0055375 A1 | 3/2007 | Ferree |
| 2007/0055377 A1 | 3/2007 | Hanson et al. |
| 2007/0067034 A1 | 3/2007 | Chirico et al. |
| 2007/0067035 A1 | 3/2007 | Falahee |
| 2007/0093897 A1 | 4/2007 | Gerbec et al. |
| 2007/0093899 A1 | 4/2007 | Dutoit et al. |
| 2007/0112428 A1 | 5/2007 | Lancial |
| 2007/0118222 A1 | 5/2007 | Lang |
| 2007/0123986 A1 | 5/2007 | Schaller |
| 2007/0162044 A1 | 7/2007 | Marino |
| 2007/0162135 A1 | 7/2007 | Segal et al. |
| 2007/0173824 A1 | 7/2007 | Rosen |
| 2007/0173830 A1 | 7/2007 | Rosen |
| 2007/0173939 A1 | 7/2007 | Kim et al. |
| 2007/0173940 A1 | 7/2007 | Hestad et al. |
| 2007/0208423 A1 | 9/2007 | Messerli et al. |
| 2007/0213717 A1 | 9/2007 | Trieu et al. |
| 2007/0225703 A1 | 9/2007 | Schmitz et al. |
| 2007/0233260 A1 | 10/2007 | Cragg |
| 2007/0239162 A1 | 10/2007 | Bhatnagar et al. |
| 2007/0244485 A1 | 10/2007 | Greenhalgh et al. |
| 2007/0255408 A1 | 11/2007 | Castleman et al. |
| 2007/0255409 A1 | 11/2007 | Dickson et al. |
| 2007/0260270 A1 | 11/2007 | Assell et al. |
| 2007/0260315 A1 | 11/2007 | Foley et al. |
| 2007/0270956 A1 | 11/2007 | Heinz |
| 2007/0270968 A1 | 11/2007 | Baynham et al. |
| 2007/0276377 A1 | 11/2007 | Yundt |
| 2007/0288028 A1 | 12/2007 | Gorensek et al. |
| 2008/0015694 A1 | 1/2008 | Tribus |
| 2008/0021558 A1 | 1/2008 | Thramann |
| 2008/0021559 A1 | 1/2008 | Thramann |
| 2008/0071356 A1 | 3/2008 | Greenhalgh et al. |
| 2008/0077150 A1* | 3/2008 | Nguyen ............ 606/85 |
| 2008/0125865 A1 | 5/2008 | Abdelgany |
| 2008/0133012 A1 | 6/2008 | McGuckin |
| 2008/0140082 A1 | 6/2008 | Erdem et al. |
| 2008/0140207 A1 | 6/2008 | Olmos et al. |
| 2008/0147193 A1 | 6/2008 | Matthis et al. |
| 2008/0147194 A1 | 6/2008 | Grotz et al. |
| 2008/0183204 A1 | 7/2008 | Greenhalgh et al. |
| 2008/0188941 A1 | 8/2008 | Grotz |
| 2008/0208255 A1 | 8/2008 | Siegal |
| 2008/0221687 A1 | 9/2008 | Viker |
| 2008/0243254 A1 | 10/2008 | Butler |
| 2008/0243255 A1 | 10/2008 | Butler et al. |
| 2008/0249625 A1 | 10/2008 | Waugh et al. |
| 2008/0249628 A1 | 10/2008 | Altarac et al. |
| 2008/0294205 A1 | 11/2008 | Greenhalgh et al. |
| 2008/0312743 A1 | 12/2008 | Vila et al. |
| 2008/0312744 A1 | 12/2008 | Vresilovic et al. |
| 2009/0005871 A1 | 1/2009 | White et al. |
| 2009/0018524 A1 | 1/2009 | Greenhalgh et al. |
| 2009/0024204 A1 | 1/2009 | Greenhalgh et al. |
| 2009/0024217 A1 | 1/2009 | Levy et al. |
| 2009/0054991 A1 | 2/2009 | Biyani et al. |
| 2009/0076511 A1 | 3/2009 | Osman |
| 2009/0143859 A1 | 6/2009 | McClellan et al. |
| 2009/0149956 A1 | 6/2009 | Greenhalgh et al. |
| 2009/0163918 A1 | 6/2009 | Levy et al. |
| 2009/0182336 A1 | 7/2009 | Brenzel et al. |
| 2009/0182431 A1 | 7/2009 | Butler et al. |
| 2009/0198338 A1 | 8/2009 | Phan |
| 2009/0234398 A1 | 9/2009 | Chirico et al. |
| 2009/0240335 A1 | 9/2009 | Arcenio et al. |
| 2009/0318928 A1 | 12/2009 | Purcell et al. |
| 2010/0004750 A1 | 1/2010 | Segal et al. |
| 2010/0004751 A1 | 1/2010 | Segal et al. |
| 2010/0016905 A1 | 1/2010 | Greenhalgh et al. |
| 2010/0082109 A1 | 4/2010 | Greenhalgh et al. |
| 2010/0125274 A1 | 5/2010 | Greenhalgh et al. |
| 2010/0168862 A1 | 7/2010 | Edie et al. |
| 2010/0262147 A1 | 10/2010 | Siegal et al. |
| 2010/0292796 A1 | 11/2010 | Greenhalgh et al. |
| 2011/0009969 A1 | 1/2011 | Puno |
| 2011/0029083 A1 | 2/2011 | Hynes et al. |
| 2011/0054621 A1 | 3/2011 | Lim |
| 2011/0087296 A1 | 4/2011 | Reiley et al. |
| 2011/0106260 A1 | 5/2011 | Laurence et al. |
| 2011/0125266 A1 | 5/2011 | Rodgers et al. |
| 2011/0184519 A1 | 7/2011 | Trieu |
| 2011/0257684 A1 | 10/2011 | Sankaran |
| 2011/0282387 A1 | 11/2011 | Suh et al. |
| 2011/0319898 A1 | 12/2011 | O'Neil et al. |
| 2011/0320000 A1 | 12/2011 | O'Neil et al. |
| 2012/0004731 A1 | 1/2012 | Viker |
| 2012/0071980 A1 | 3/2012 | Purcell et al. |

FOREIGN PATENT DOCUMENTS

| | | |
|---|---|---|
| EP | 1804733 | 7/2007 |
| FR | 2874814 | 11/2007 |
| FR | 2900814 | 11/2007 |
| JP | 2000-210315 | 8/2000 |
| JP | 2002-535080 | 10/2002 |
| JP | 2003-512887 | 4/2003 |
| JP | 2004-511297 | 4/2004 |
| JP | 2004-531355 | 10/2004 |
| JP | 2004-321348 | 11/2004 |
| SU | 662082 | 5/1979 |
| WO | WO 88/03781 | 6/1988 |
| WO | WO 92/14423 | 9/1992 |
| WO | WO 95/31945 | 11/1995 |
| WO | WO 96/03092 | 2/1996 |
| WO | WO 97/00054 | 1/1997 |
| WO | WO 00/30523 | 6/2000 |
| WO | WO 00/44319 | 8/2000 |
| WO | WO 00/44321 | 8/2000 |
| WO | WO 01/32099 | 5/2001 |
| WO | WO 01/78625 | 10/2001 |
| WO | WO 01/95838 | 12/2001 |
| WO | WO 02/13700 | 2/2002 |
| WO | WO 02/32347 | 4/2002 |
| WO | WO 03/003943 | 1/2003 |
| WO | WO 03/003951 | 1/2003 |
| WO | WO 2005/062900 | 7/2005 |
| WO | WO 2005/096975 | 10/2005 |
| WO | WO 2005/120400 | 12/2005 |
| WO | WO 2006/023514 | 3/2006 |
| WO | WO 2006/023671 | 3/2006 |
| WO | WO 2006/026425 | 3/2006 |
| WO | WO 2006/028971 | 3/2006 |
| WO | WO 2006/034396 | 3/2006 |
| WO | WO 2006/034436 | 3/2006 |
| WO | WO 2006/037013 | 4/2006 |
| WO | WO 2006/042334 | 4/2006 |
| WO | WO 2006/050500 | 5/2006 |
| WO | WO 2006/060420 | 6/2006 |
| WO | WO 2006/072941 | 7/2006 |
| WO | WO 2006/076712 | 7/2006 |
| WO | WO 2006/086241 | 8/2006 |
| WO | WO 2006/096167 | 9/2006 |
| WO | WO 2006/116761 | 11/2006 |
| WO | WO 2006/132945 | 12/2006 |
| WO | WO 2007/009107 | 1/2007 |
| WO | WO 2007/009123 | 1/2007 |
| WO | WO 2007/016368 | 2/2007 |
| WO | WO 2007/038611 | 4/2007 |
| WO | WO 2007/041698 | 4/2007 |
| WO | WO 2007/047098 | 4/2007 |
| WO | WO 2007/050322 | 5/2007 |
| WO | WO 2007/056433 | 5/2007 |
| WO | WO 2007/062080 | 5/2007 |
| WO | WO 2007/075411 | 7/2007 |

(56) References Cited

FOREIGN PATENT DOCUMENTS

| | | |
|---|---|---|
| WO | WO 2007/079021 | 7/2007 |
| WO | WO 2007/084257 | 7/2007 |
| WO | WO 2007/084268 | 7/2007 |
| WO | WO 2007/084810 | 7/2007 |
| WO | WO 2007/100591 | 9/2007 |
| WO | WO 2007/123920 | 11/2007 |
| WO | WO 2007/124130 | 11/2007 |
| WO | WO 2007/126622 | 11/2007 |
| WO | WO 2007/130699 | 11/2007 |
| WO | WO 2007/131026 | 11/2007 |
| WO | WO 2007/133608 | 11/2007 |
| WO | WO 2007/140382 | 12/2007 |
| WO | WO 2008/005627 | 1/2008 |
| WO | WO 2008/016598 | 2/2008 |
| WO | WO 2008/070863 | 6/2008 |
| WO | WO 2009/114381 | 9/2009 |
| WO | WO 2009/130824 | 10/2009 |
| WO | WO 2012/027490 | 3/2012 |

OTHER PUBLICATIONS

Pyo, R. et al., "Targeted Gene Disruption of Matrix Metalloproteinase-9 (Gelatinase B) Suppresses Development of Experimental Abdominal Aortic Aneurysms," *J. Clinical Investigation*, 105(11):1641-1649, June 2000.

Tambiah, J. et al., "Provocation of Experimental Aortic Inflammation Mediators and *Chlamydia pneumoniae*," *Brit., J. Surgery*, 88(7):935-940, Feb. 2001.

Walton, L.J. et al., "Inhibition of Prostoglandin E2 Synthesis in Abdonminal Aortic Aneurysms," *Circulation*, 48-54, Jul. 6, 1999.

Xu, Q. et al., "Sp1 Increases Expression of Cyclooxygenase-2 in Hypoxic Vascular Endothelium," *J. Biological Chemistry*, 275(32)24583-24589, Aug. 2000.

Database WPI, Week 198004, Thomson Scientific, London, GB; AN 1980-A8866C, XP002690114, -& SU 662 082 A1 (Tartus Univ) May 15, 1979, abstract, figures 1,2.

Choi, G. et al., "Percutaneous Endoscopic Lumbar Discemtomy by Transiliac Approach," *Spine* 34(12)E443-446, May 20, 2009.

\* cited by examiner

NOT INVENTION

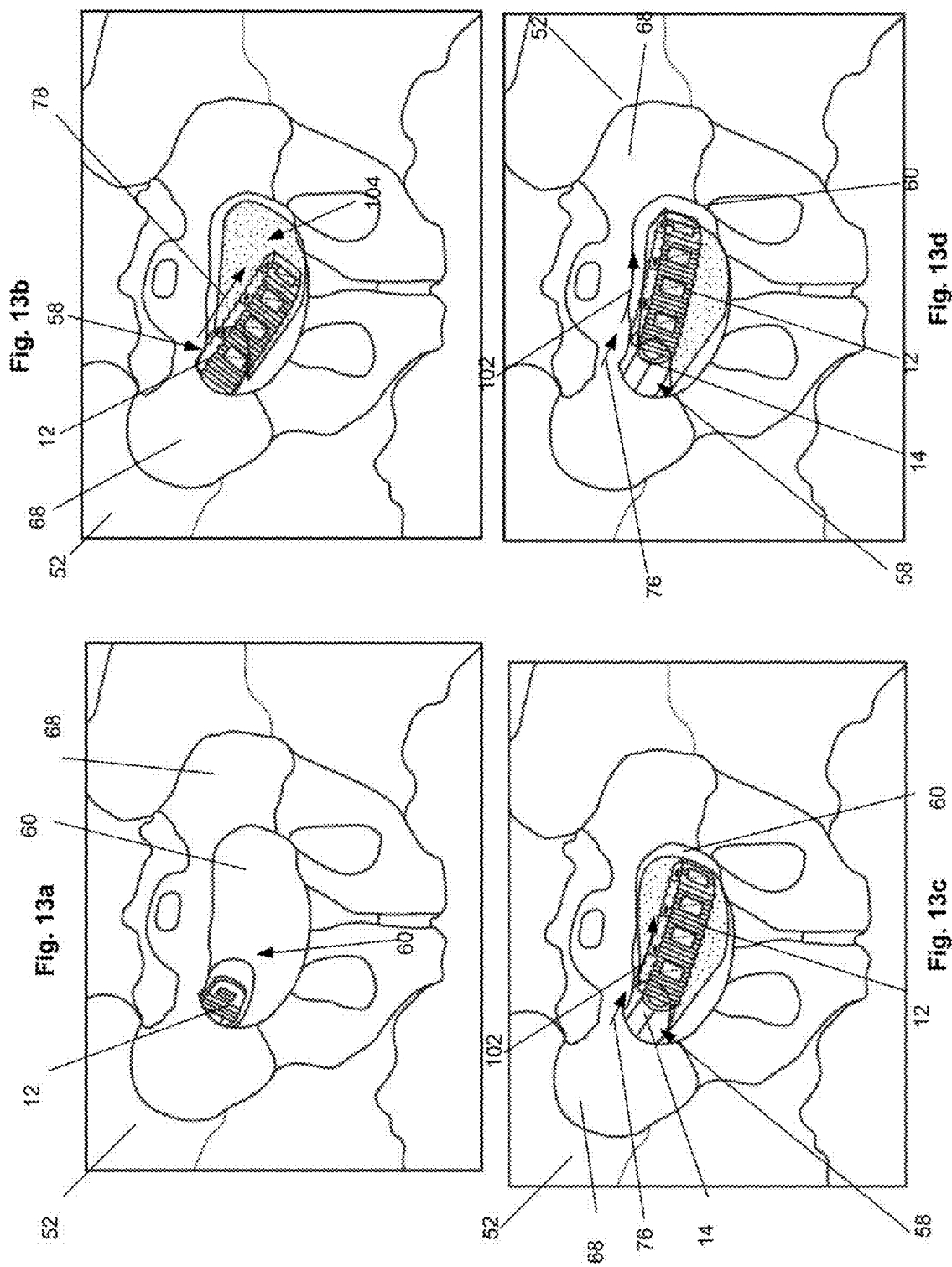

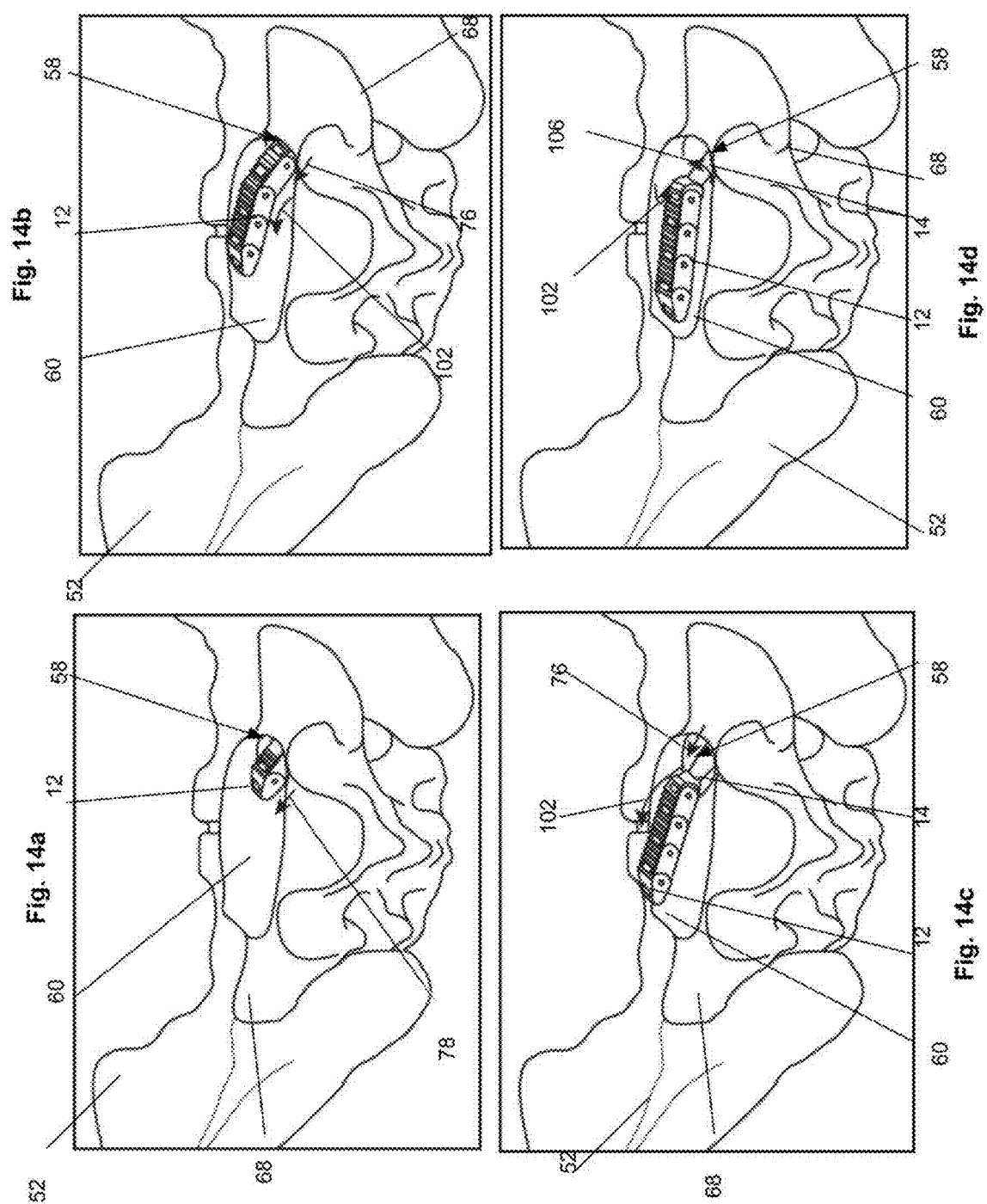

TISSUE REMOVAL DEVICE AND METHOD

CROSS-REFERENCE TO RELATED APPLICATIONS

The present application claims priority to U.S. Provisional Application No. 61/526,630 filed 23 Aug. 2011 which is incorporated by reference herein in its entirety.

BACKGROUND

Existing surgery to treat spinal ailments includes the removal of intervertebral discs, known as a discectomy. The removed discs can be replaced by other devices including rigid metal implants.

Discectomies performed between the L5 and S1 vertebrae are difficult because the path to access the L5-S1 intervertebral space often passes through tissue in front of the sacrum which contains a large quantity of sensitive nerves and arteries. There is a substantial risk of serious damage caused as a side effect of the discectomy and the delivery of the implant to the L5-S1 intervertebral space.

There exists a method for creating a delivery channel through the hone of the iliac and/or sacrum to deliver the implant. However, manipulating, positioning and orienting the implant on the medial side of the channel is not easy. Also, unintended soft tissue damage is still possible when a device is exiting the hone channel and traverses soft tissue before entering the intervertebral space. Furthermore, performing the discectomy is difficult if not impossible through the channel because access to the disc space is constrained through the channel.

Accordingly, a method and device for performing a discectomy through and on the far side of a transosseous or other constrained channel is desired.

SUMMARY OF THE INVENTION

Devices for removing tissue are disclosed. The device can have a rigid shaft attached to an articulating broach. The broach can have a tapered distal terminal tip. The broach can have teeth extending laterally or radially from the broach.

The broach can have a first segment longitudinally distal to a second segment. The first segment can be rotatably attached to the second segment. The broach can have a third segment longitudinally proximal to the second segment. The third segment can be rotatably attached to the second segment. The third segment can be attached to the rigid shaft.

A method for removing tissue from a biological target site is also disclosed. The method includes inserting the multi-segmented articulating broach into the target site. The method can include forming a channel through an obstructing bone, such as the iliac and/or sacral ala. The channel can have an exit port in the S1 endplate. The broach can be translated into and out of the channel. The broach can be articulated while the broach is located at the target site.

The broach can capture tissue debris at the target site and can be removed from the target site. When the broach is removed from the target site, the broach can remove tissue debris from the target site. The method can be performed, for example, in the L5-S1 intervertebral disc space.

BRIEF DESCRIPTION OF THE DRAWINGS

FIGS. 13a through 13d illustrate a superior view of a variation ( ) a method of using the tissue removal device anatomically showing the iliac and sacrum, but not the L5-S1 disc or remainder of the spine for illustrative purposes.
FIGS. 14a through 14d illustrate a posterior perspective view of a variation eta method of using the tissue removal device anatomically showing the iliac and sacrum, but not the L5-S1 disc or remainder of the spine for illustrative purposes.

DETAILED DESCRIPTION

Figure 1:
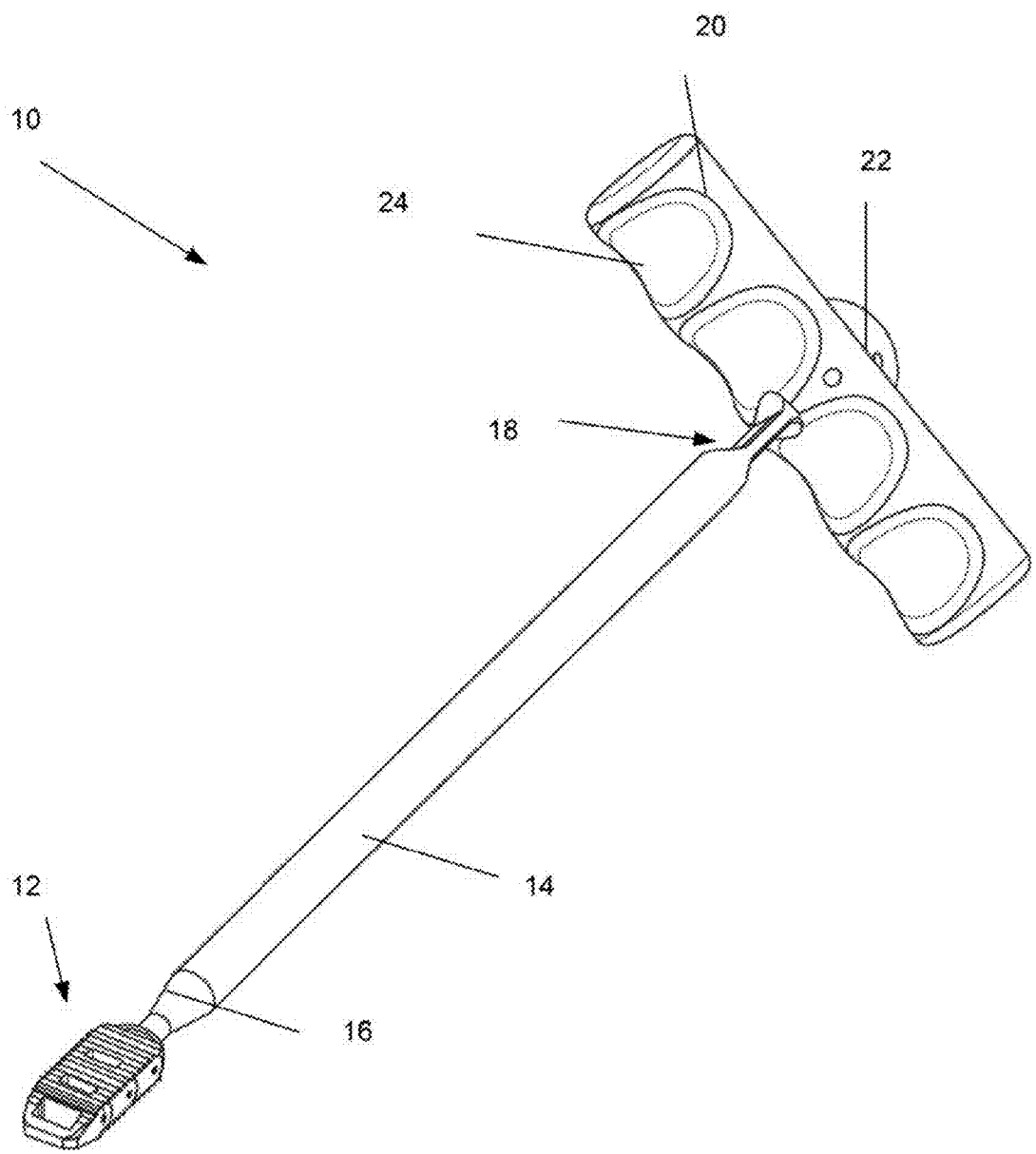
FIG. 1 illustrates a variation of the tissue removal device.

FIG. 1 illustrates that a tissue removal tool 10 or device can have a broach 12, auger, or borer attached to the distal end of a shaft. The tool 10 can be configured to remove hard tissue and or soil tissue, such as bone, cartilage, ligaments, collagenous tissue such as intervertebral discs, infected tissue, or combinations thereof from a target site inside of a patient's body. The tool 10 can be configured to remove the tissue through a tunnel or channel formed in the patient's body.

The broach 12 can be rigid, flexible, fixed (i.e., unarticulatable), articulatable within the broach 12 and/or at the broach's connection with the shaft 14, or combinations thereof. The distal terminal end of the broach 12 can be traumatically or atraumatically sharpened and/or pointed, for example to dissect tissue when pushed through the tissue. Part or all of the broach surface can be smooth and/or textured. The shaft 14 can taper at a shaft taper 16 to the broach 12.

The shaft 14 can be rigid or flexible along the entire length, or have alternating flexible and rigid lengths. The shaft 14 can be unitary and unarticulatable or jointed and articulatable. The shaft 14 can have control rods (not shown) disposed within or outside of the shaft 14 to control articulation (e.g., lock and unlock articulation, and to control the angles of articulation for each joint) of the broach 12.

The distal terminal end of the shaft 14 can taper at a shaft taper 16 to a connection with the broach 12. The distal end of the shaft 14 can be fixably or removably attached to the broach 12.

The proximal end of the shaft 14 can taper to a shaft neck 18. The proximal end of the shaft 14 can attach to or be integral with a handle 20. The handle 20 can have one, two, three, tour or five finger (and thumb) seats 24, for example to ergonomically confirm to the user's hand along with the shaft neck 18. The handle 20 can have articulating control surfaces, such as buttons, switches or triggers in one or more of the finger seats 24. The articulating control surfaces can control the articulation, attachment, detachment, or combinations thereof of the broach 12 with respect to the distal end of the shaft 14.

The proximal terminal end of the shaft 14 can have a shaft head 22. The shaft head can be fixed to or removable from the remainder of the shaft 14. The shaft head 22 can be removed from the remainder of the shaft 14, for example, allowing removal and replacement of the handle 20 (e.g., to replace the handle 20 with a larger or smaller handle 20 to fit the user's hand). The shaft 14 can be attached, for example at the shaft head 22, to auxiliary devices not shown. The auxiliary devices can be or have an electronic, hydraulic or pneumatic supersonic, hypersonic or subsonic oscillator; a power and/or control unit configured to articulate the broach 12; visualization and lighting devices for delivering and receiving visualization and lighting power and signals to and from the distal end of the shaft 14 and/or the broach 12; aspiration and/or irrigation tools for delivering and receiving solids and fluids (e.g., saline, analgesics, anesthetic, antibiotics, debris) to and from the distal end of the shaft 14 and/or the broach 12 or combinations thereof.

Figure 2:
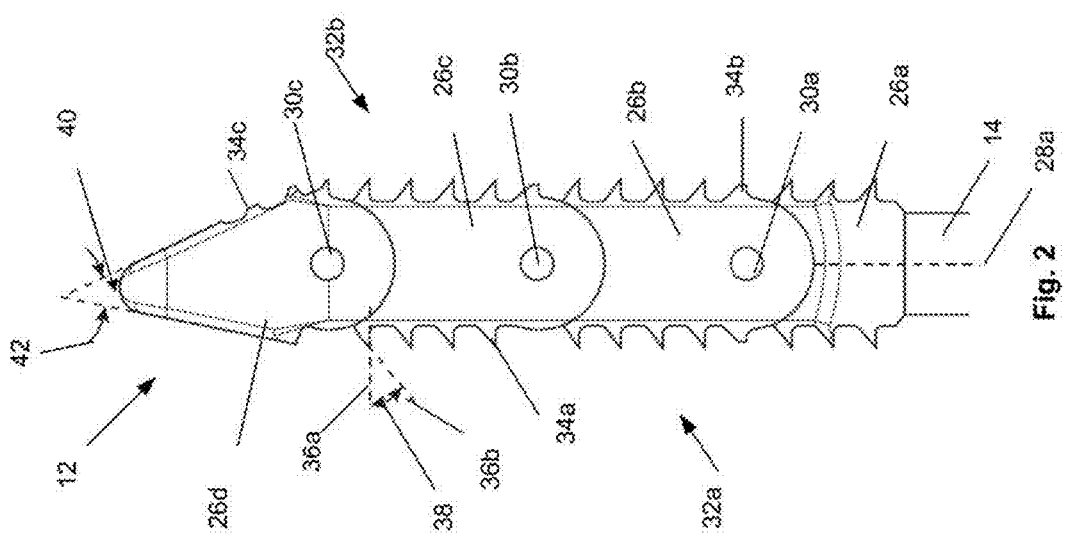
FIG. 2 is a side view of a variation of the broach in an unarticulated configuration.

FIG. 2 illustrates that the broach 12 can have a connecting segment 26a fixedly 6 or rotatably attached to the shaft 14. The connecting segment 26a can have a connecting segment longitudinal axis 28a. The connecting segment 26a can be fixed to or rotate with respect to the shaft 14 around the connecting segment longitudinal axis 28a and/or around one or more axes perpendicular to the connecting segment longitudinal axis 26a.

The broach 12 can have a second trailing segment 26b. The second trailing segment 26b can have a second trailing hinge 30a at the proximal end of the second trailing segment 26b. The second trailing, segment 26b can be rotatably attached to the connecting segment 26a at the second trailing hinge 30a.

The broach 12 can have a first trailing segment 26c. The first trailing segment 26c can have a first trailing hinge 30b at the proximal end of first trailing, segment 26c. The first trailing segment 26c can be rotatably attached to the second trailing segment 26b at the first trailing hinge 30b.

The broach 12 can have a distal segment 26d at the distal terminal end of the broach 12. The distal segment 26d can have a lead hinge 26c at the proximal end of the distal segment 26d. The distal segment 26d can be rotatably attached to the first trailing segment 26c at the lead hinge 26c.

The broach 12 can have zero, one, three, four or more trailing segments 26 rotatably connected in series, similar to the configuration shown in FIG. 2, between the distal or lead segment 26d and the connecting segment 26a or shaft 14.

The first trailing hinge 30b, second trailing hinge 30a and lead hinge 30c can be in the same (as shown) or different planes when the broach 12 is in a linear configuration, as shown in FIG. 2.

The broach 12 can have an inferior side 32a and a superior side 32b. During use, the inferior side 32a can face the inferior end of the patient and the superior side 32b can face the superior end of the patient.

Any or all segments 26 of the broach 12 can have one or more teeth 34 on the inferior and/or superior sides 32a and/or 32b of the broach 12. Any or all segments 26 of the broach 12 can have one or more teeth 34 on the lateral sides of the broach, for example on perpendicular planes to the inferior and superior sides 32a and 32b. The segments 26 can have face teeth 34a and hinge teeth 34b. The face teeth 34a can be equivalent or differently shaped than the hinge teeth 34b. The face teeth 34a can be shaped and located symmetrically compared with teeth 34 on the opposite side of the broach 12 or asymmetrically shaped or located compared with teeth 34 on the opposite side of the broach 12. The hinge teeth 34b can be on one side of the broach 12, for example on the superior side 32b of the broach 12, but no hinge tooth 34b can be positioned on the inferior side 32a of the broach 12 at the same length along the broach 12 as the corresponding hinge tooth 34b, as shown. The hinge teeth 34b can correspond in length to the position of the hinge 30. Each segment 26 can have one, two, three, four (as shown), five or more face teeth 34a on one or each (as shown) side of the segment 26.

Each face tooth 34a can have a hinge tooth leading face 36a and a face tooth trailing face 36b. Each hinge tooth can have a hinge tooth leading face and a hinge tooth trailing face that can be analogous to the face tooth leading face 36a and the face tooth trailing lace 36b, respectively. The teeth 34 can have a face or hinge tooth angle 38 formed between the tooth leading face and the tooth trailing face. The tooth angles 38 can be from about 3° to about 90°, more narrowly from about 10° to about 45°, for example about 25°.

The teeth 34 can have flat trailing faces or concave trailing faces. The teeth 34 can have flat leading faces or convex leading faces.

The trailing faces can be perpendicular to the longitudinal axis of the respective segment or pointed in a proximal direction. The teeth 34 can be unidirectional, providing less resistance when the broach 12 is pushed distally against tissue and more resistance when the broach 12 is pulled proximally against tissue.

The distal segment 26d can have lead teeth 34c. The lead teeth 34c can be configured identically to the face or hinge teeth 34a or 34b or can be smaller. For example, the lead teeth 34x can have a flatted radially distal tip. The lead teeth 34c can be on the superior and/or inferior sides of the distal segment 26d.

Any or all of the teeth 34 can be configured to produce less three resistance when the broach 12 is pushed distally through tissue and more forced resistance when the broach 12 is pulled proximally through tissue. For example, the lace tooth leading face 36a can be perpendicular to the longitudinal axis of the respective segment 26, and the face tooth trailing face 36b can extend proximally as the face tooth trailing face 36b extends away from the segment 26. The teeth 34 can be configured to separate and remove tissue when the broach 12 is pushed distally through tissue and to not or minimally separate and remove tissue when the broach 12 is pulled proximally through tissue.

The distal terminal end of the distal segment 26d can have a distal tip 40. The distal segment 26d can taper to the distal tip 40. The inferior and/or superior faces of the distal segment 26d can be flat and/or convex and/or concave. The distal tip 40 can be flat, a bullet tip, or a chisel tip (as shown).

The distal tip 40 can form a distal tip angle 42. The distal tip angle 42 can be measured as the intersecting angle between the plane of the face of the interior side of the distal segment 26d and the plane of the face of the superior side of the distal segment 26d. The distal tip angle 42 can be from about 1° to about 90°, more narrowly from about 3° to about 45°, yet more narrowly from about 5° to about 35°, yet more narrowly from about 15° to about 30°.

Figure 3:
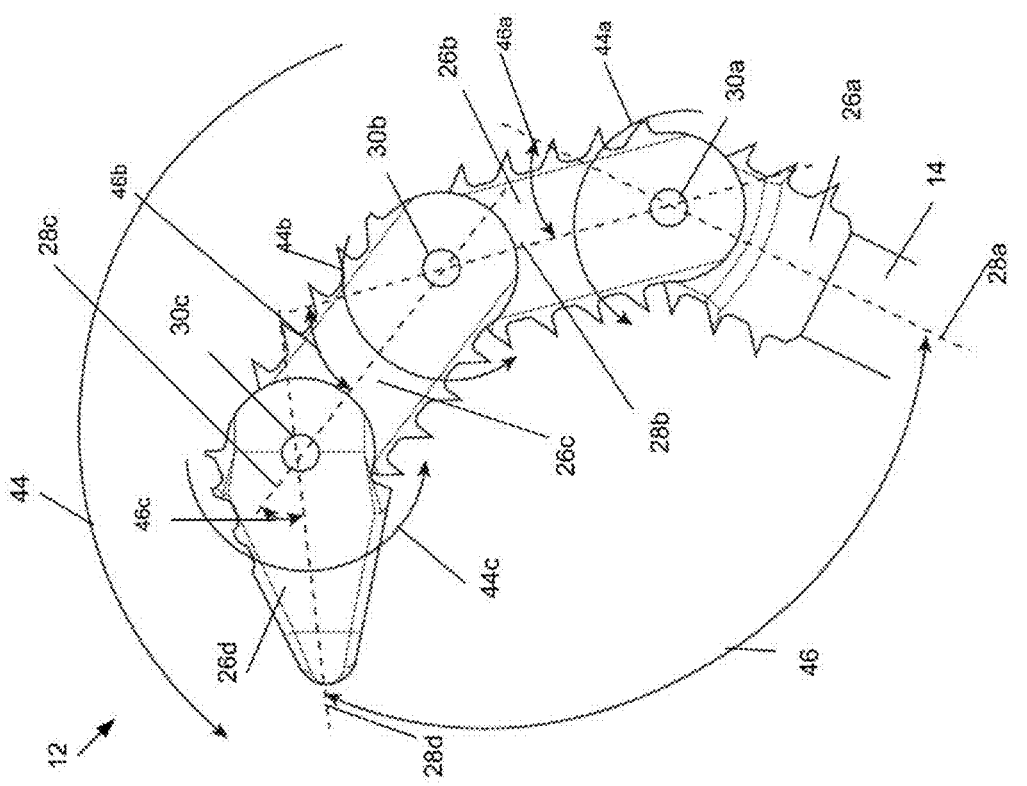
FIG. 3 is a side view of the broach of FIG. 2 in an articulated configuration.

FIG. 3 illustrates that the broach 12 can be articulated, as shown by arrow 44. The connecting segment longitudinal axis 28a can be collinear with the shaft longitudinal axis.

The broach 12 can articulate at a broach articulation angle 46. The broach articulation angle 46 can be measured between the connecting segment longitudinal axis 28a and the distal segment longitudinal axis 28d. The broach articulation angle 46 can be about 180° as shown in FIG. 2. The broach articulation angle 46 can be controlled to be a minimum of about 155°, yet more narrowly about 135°, yet more narrowly about 90°, yet more narrowly about 60°, yet more narrowly about 45°.

The distal segment 26d can have a distal segment longitudinal axis 28d. The first trailing segment 26c can have a first trailing segment longitudinal axis 28c. The second trailing segment 26b can have a second trailing segment longitudinal axis 28b.

The second trailing segment 26b can articulate about the second trailing hinge 30a with respect to the connecting segment 26a, as shown by arrow 44a. The second trailing segment longitudinal axis 28b can form a second trailing segment articulation angle 46a with respect to the connecting segment longitudinal axis 28a. The second trailing segment articulation angle 46a can be about 180° as shown in FIG. 1. The second trailing segment articulation angle 46a can be controlled to be a minimum of about 155°, yet more narrowly about 135°, yet more narrowly about 90°, yet more narrowly about 60°, yet more narrowly about 45°.

The first nailing segment 26e can articulate about the first trailing, hinge 30b with respect to the second trailing segment 26d, as shown by arrow. The first trailing segment longitudinal axis 28c can form a first trailing segment articulation angle 46b with respect to the second trailing segment longitudinal axis 28a. The first trailing segment articulation angle 46b can be about 180° as shown in FIG. 1. The second trailing segment articulation angle 46b can be controlled to be a minimum of about 155°, yet more narrowly about 135°, yet more narrowly about 90°, yet more narrowly about 60°, yet more narrowly about 45°.

The distal segment 26d can articulate about the lead hinge 30c with respect to the first trailing segment 26c, as shown by arrow. The distal segment longitudinal axis 28d can form a distal segment articulation angle 46c with respect to the first trailing segment longitudinal axis 28c. The distal segment articulation angle 46c can be about 180° as shown in FIG. 1. The distal segment articulation angle 46c can be controlled to be a minimum of about 155°, yet more narrowly about 135°, yet more narrowly about 90°, yet more narrowly about 60°, yet more narrowly about 45°.

The hinges 30 can be perpendicular to the longitudinal axes 28 of the respective segments 26.

Figure 4:
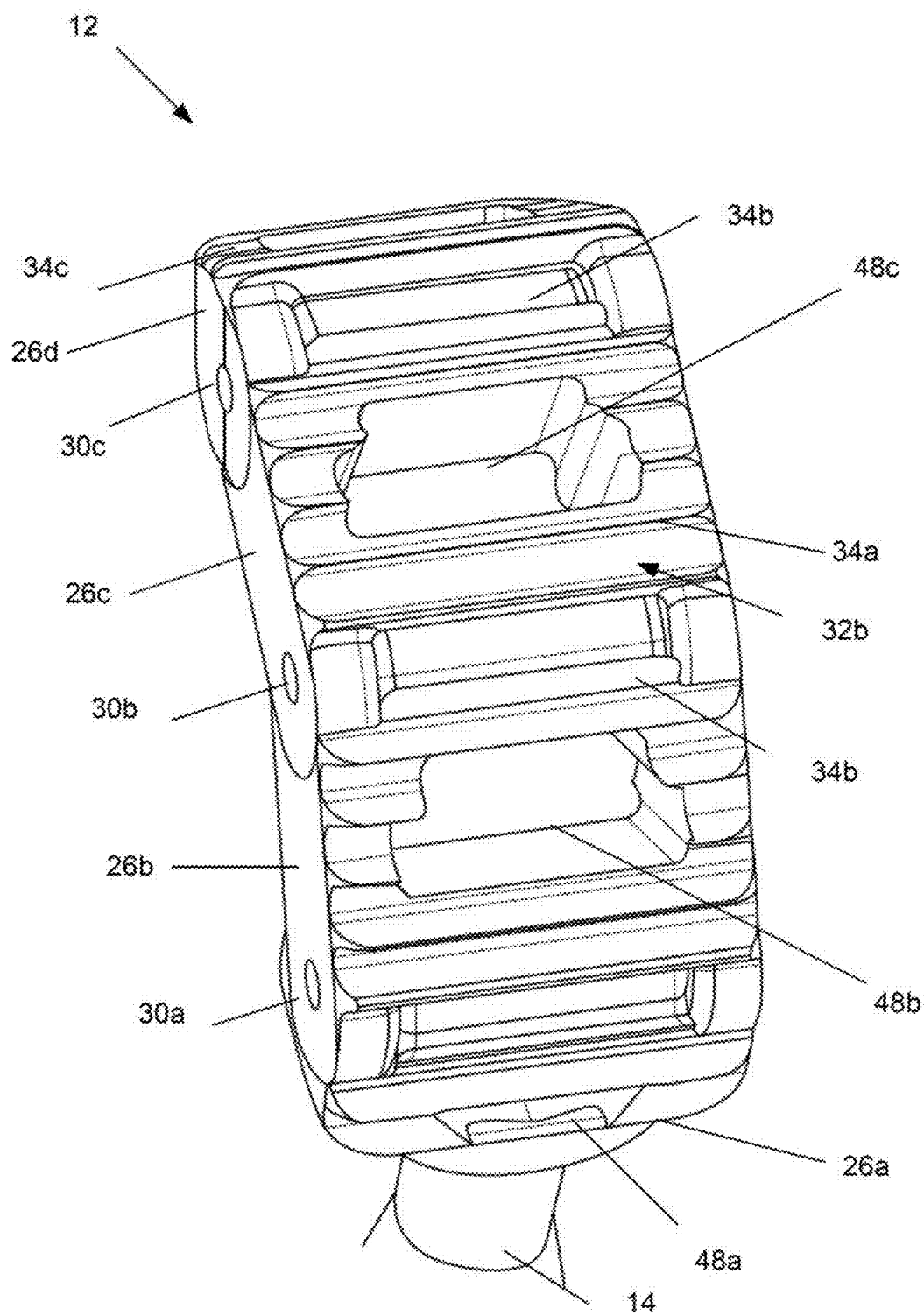
FIG. 4 is a perspective view of a variation of the broach in an articulated configuration.

FIG. 4 illustrates that the connecting segment 26a can have one or more connecting segment through ports 48a. The second trailing segment 26b can have one or more second trailing segment through ports 48b. The first trailing segment 26c can have one or more first trailing, segment through ports 48c. The distal segment 26d can have one or more distal segment through ports.

Any or all of the through ports 48 can extend through the entire device or broach 12. Instead of one or more (e.g., all) of through ports 48, the broach 12 can have recesses or cavities. During use, the through ports, recesses, cavities or combinations thereof can fill with debris 82, such as hard or soft tissue debrided by the teeth 34.

Any or all of the hinges 30 can have a hinge tooth 34h extending radially away from the hinge 30 in the direction of the superior side 32b and/or inferior side 34a of the broach 12. The hinge teeth 34b can be rotatably fixed to the hinge 30 or one of the segments 26 adjacent to the respective hinge 30.

Figure 5:
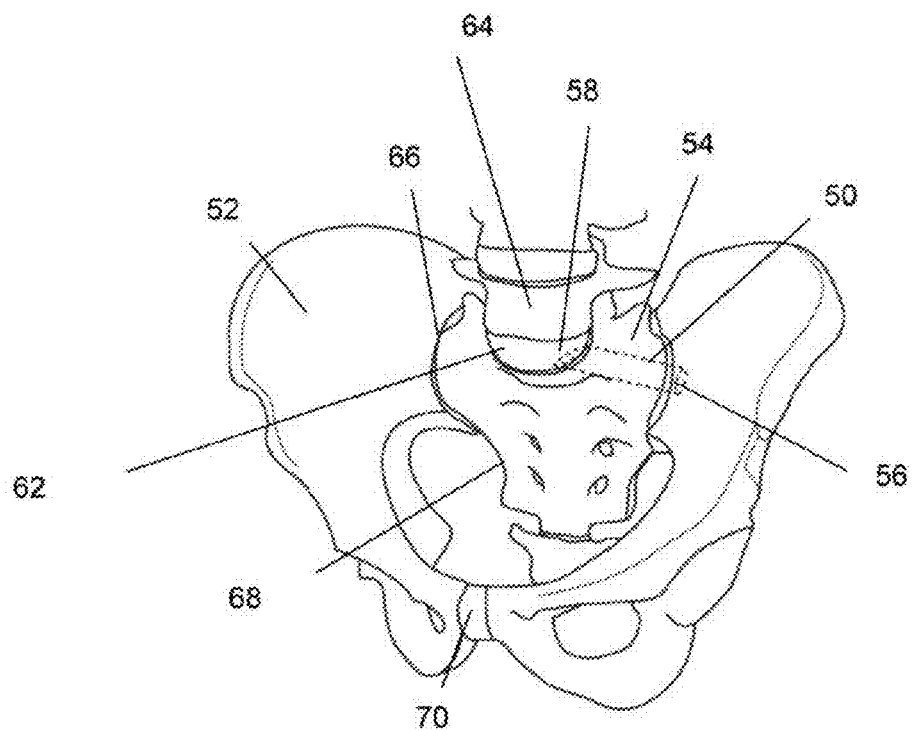
FIG. 5 illustrates the lower spine and pelvis.

FIG. 5 illustrates that a straight or curved transosseous delivery channel 50 can be drilled, chiseled, punched, or a combination thereof, through the iliac hone 52 and/or the sacral ala 54. The transosseous delivery channel 50 can have a laterally-located channel entry port 56 outside of the sacral ala 54 and/or iliac bone 52. The transosseous delivery channel 50 can have a channel exit port 58 adjacent to the L5-S1 intervertebral disc 62 space. For example, the channel exit port 58 can be in the S1 vertebral endplate 60. The channel exit port 58 can be positioned so the circumference of the channel exit port 58 tangentially coincides with or is closely adjacent to (e.g., within about 2 cm, more narrowly within about 1 cm, more narrowly within about 5 mm, yet more narrowly within about 2 mm) with the edge of the S1 vertebral endplate 60. Also shown for clarity are the L5 vertebra 64, sacroiliac joint 66, sacrum 68, and symphysis pubis 70.

Figure 6:
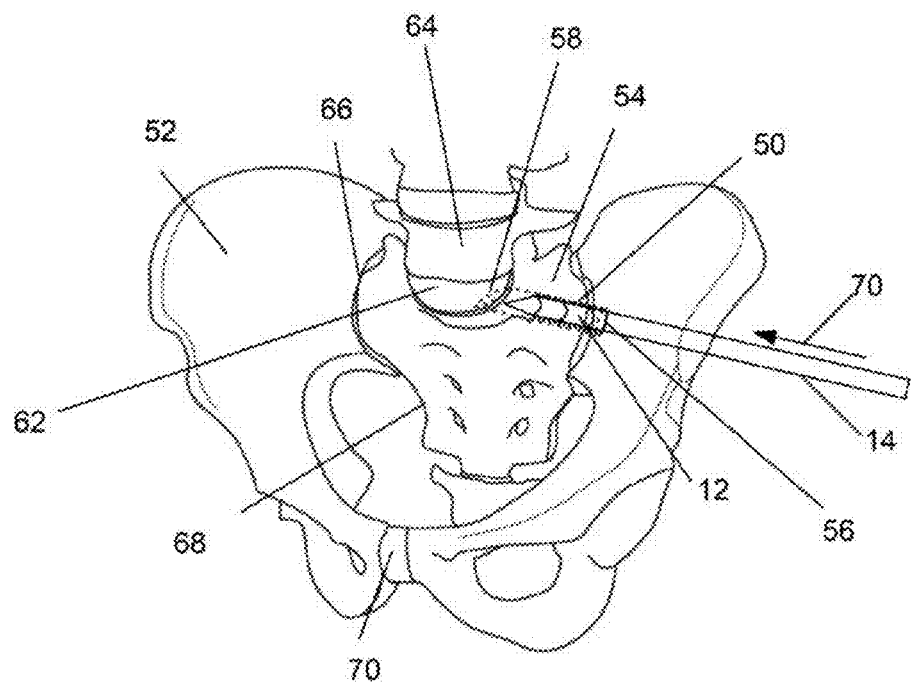
FIGS. 6 through 9 illustrate a variation of a method of using the tissue removal device.

FIG. 6 illustrates that the broach 12 of the tissue removal device 10 can be inserted, as shown by arrow 72, medially through the channel entry port 56 of the transosseous delivery channel 50.

Figure 7:
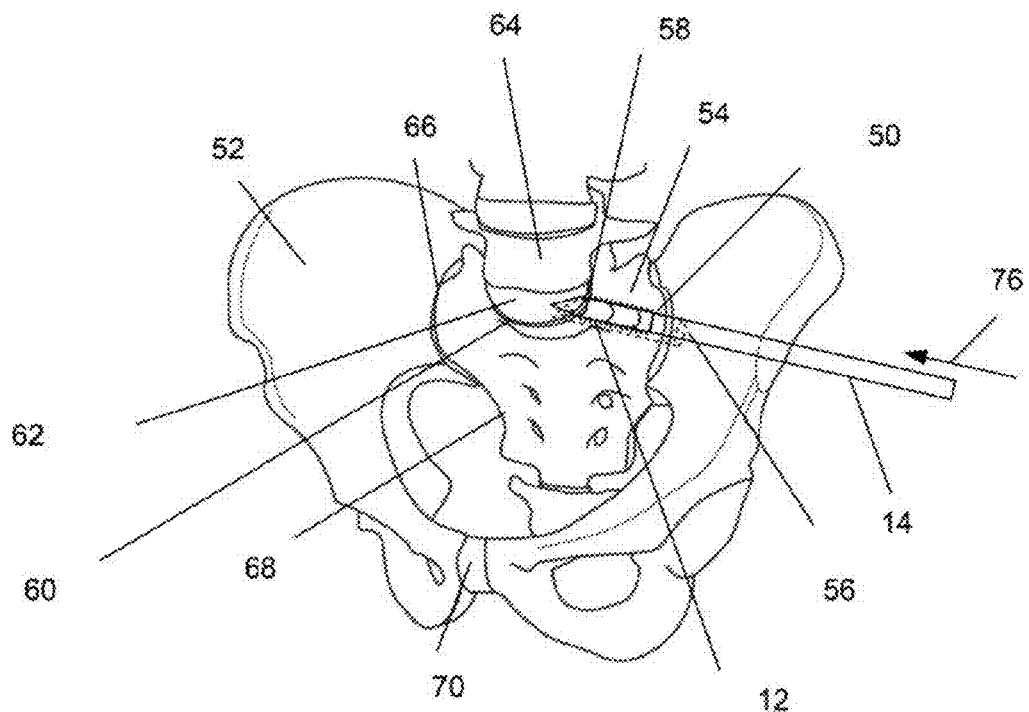

FIG. 7 illustrates that the shaft 14 can be further translated, as shown by arrow 76, into the transosseous delivery channel 50. The broach 12 can translate toward and into the L5-S1 intervertebral disc 62 space. The distal tip of the broach 12 can pierce the L5-S1 intervertebral disc 62, and/or the distal tip can wedge between the L5-S1 intervertebral disc 62 and the L5 or S1 vertebra. The broach 12 can enter the target site of the L5-S1 intervertebral disc 62 directly from the transosseous delivery channel 50 without passing through any soft tissue between the L5-S1 intervertebral disc 62 and the iliac bone 52.

Figure 8:
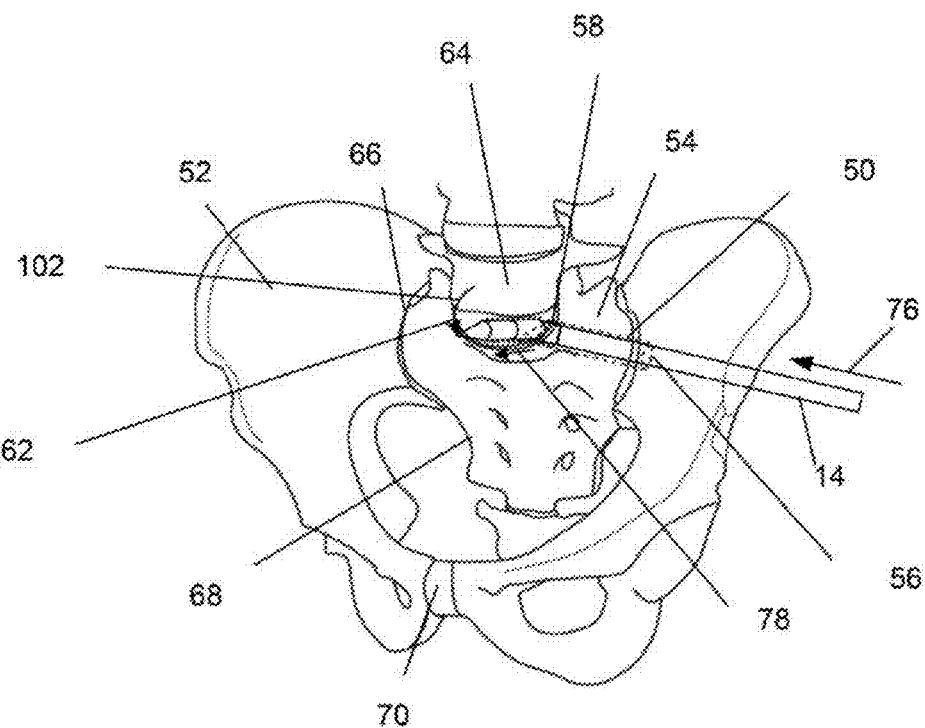

FIG. 8 illustrates that the shalt 14 can be further translated, as shown by arrow 76, medially through the transosseous delivery channel 50. The broach 12 can translate, as shown by arrow 78, through the L5-S1 intervertebral disc and/or between the L5-S1 intervertebral disc 62 and the L5 and/or the S1 vertebra. The broach 12 can articulate, as shown by arrow 102. One or more of the hinges 30 can rotate. The hinges 30 can be controllably rotatably locked and unlocked, for example, by controls on the handle 20.

The broach 12 can then be translated, such as being vibrated (e.g., manually, ultrasonically), for example, medially and laterally, and/or superior and inferiorly, and/or anteriorly and posteriorly. The through ports 48 and/or cavities and/or recesses in the broach 12 can partially and/or completely fill with soft (e.g., part or all of the L5-S1 vertebral disc) and/or hard tissue (e.g., a portion of either or both of the L5 or S1 vertebra) debris 82. The broach 12 can deliver a cauterizing electrical energy. The broach 12 and shaft 14 can have one or more longitudinal lumens that can be used to irrigate (e.g., with analgesic agents, saline, anesthetic agents, bone morphogenic proteins, visualization agents, other agents described herein, or combinations thereof) and/or aspirate (e.g., to remove irrigated material and/or debris 82) the target site (e.g., the L5-S1 intervertebral disc space).

Figure 9:
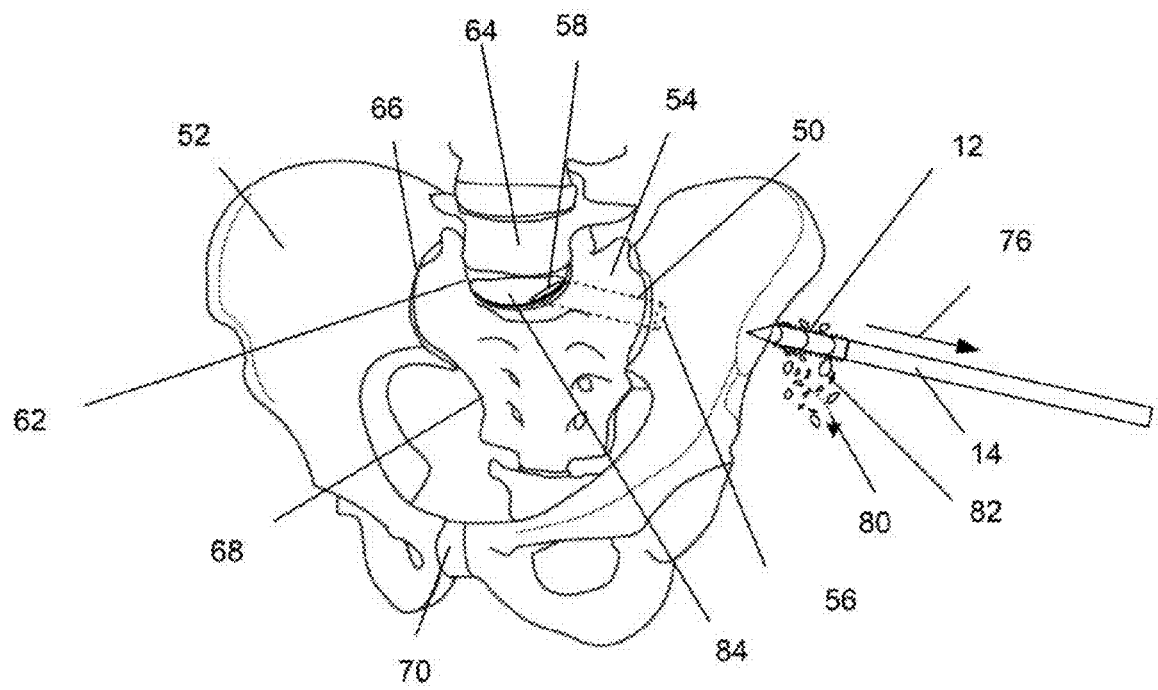

FIG. 9 illustrates that the shaft 14 can be translated laterally, for example removing the broach 12 from the L5-S1 intervertebral disc 62 space and the transosseous delivery channel 50. The debris 82 removed from the L5-S1 intervertebral disc 62 space and held by the broach 12 upon exiting the transosseous delivery channel 50 can be passively or actively removed from the through ports 48, cavities, recessesor combinations thereof, before or after the broach 12 is removed from the transosseous delivery channel 50. The removed portion of tissue can leave a partial or complete discectomy 84. The method shown in FIGS. 6 though 9 can be repeated to remove additional tissue.

Figure 10:
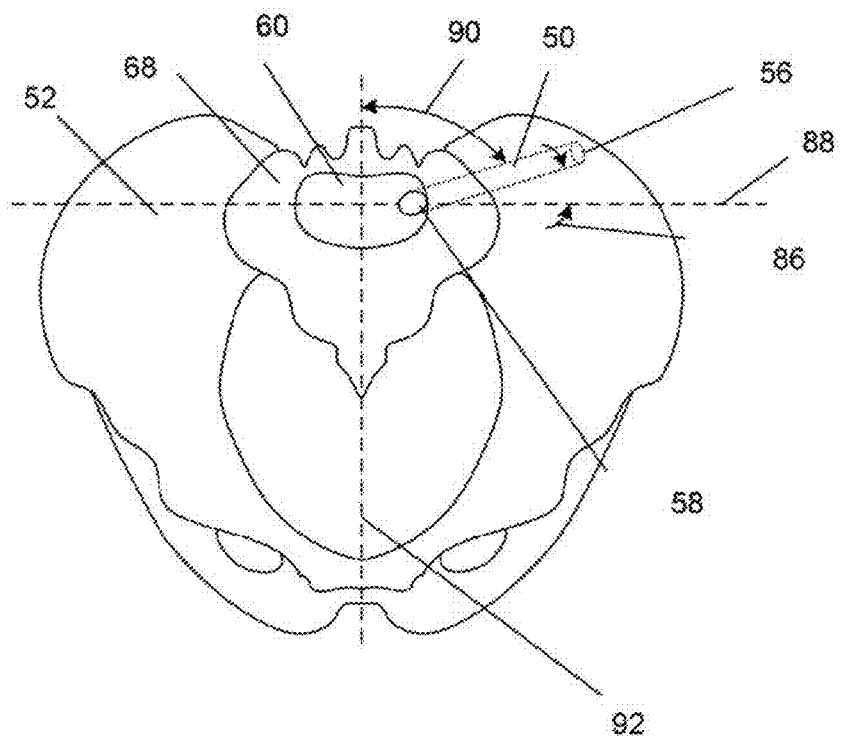
FIGS. 10 through 12 illustrate views through the transverse plane from a superior location, the sagittal plane from a lateral location, and the coronal plane from an anterior location, respectively, of a variation of the location of the transosseous delivery channel.
Figure 11:
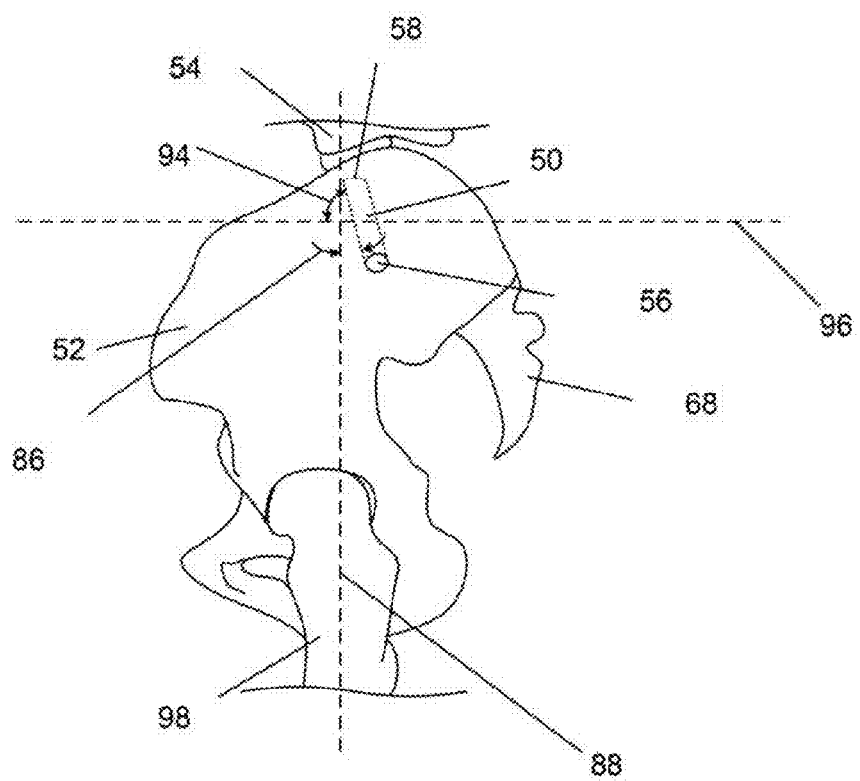
Figure 12:
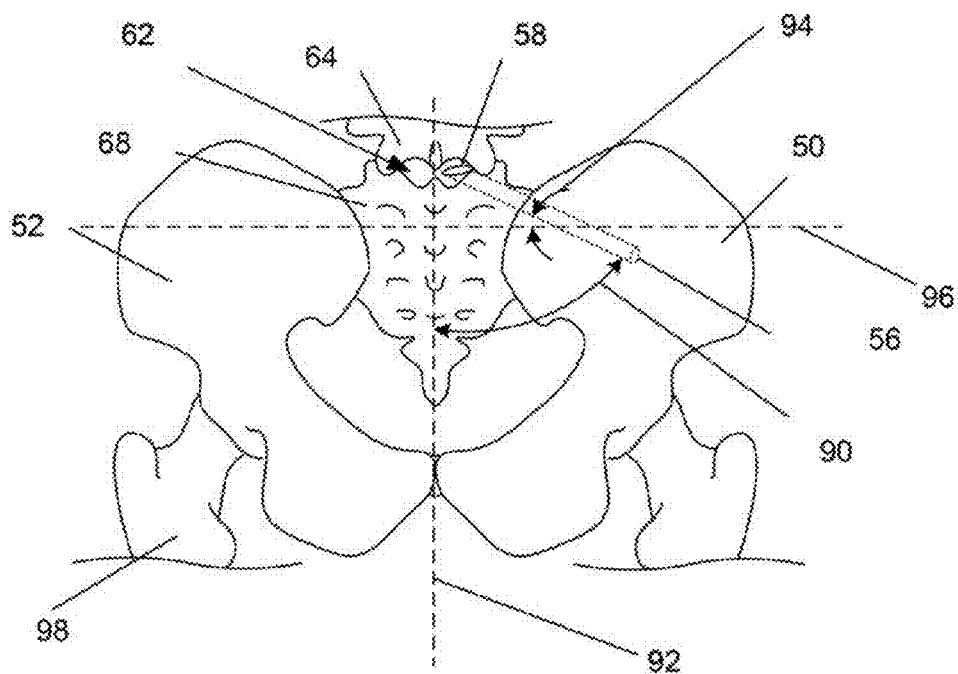

FIGS. 10 through 12 illustrate that the transosseous delivery channel 50 can have a coronal delivery angle 86 measured to the coronal plane 88, a sagittal delivery angle 90 measured to the sagittal plane 92, and a transverse delivery angle 94 measured to the transverse plane 96. The coronal delivery angle 86 can be from about 0° to about 25°, for example about 12°. The sagittal delivery angle 90 can be from about 65° to about 90°, for example about 75°. The transverse delivery angle 94 can be from about 0° to about 20°, for example about 10°. The broach 12 and shaft 14 are configured so the broach 12 can exit the channel exit port 58 (e.g., directly into the L5-S1 intervertebral disc 62) and articulate sufficiently to enter and pass through all or a significant portion (e.g., more than about 40%, yet more narrowly more than about 50%, yet more narrowly more than about 75%) of the width of the L5-S1 intervertebral space. The femurs 98 are shown for illustrative purposes.

FIGS. 13a through 13d, and separately FIGS. 14a through 14e illustrate the deployment of the broach into the L5-S1 intervertebral disc space target site 104, as described for FIGS. 5-8.

FIG. 14d illustrates the shaft can be rotated about the longitudinal axis of the shaft 14 before during or after the broach 12 is positioned in the L5-S1 intervertebral disc 62 space target site. The broach 12 can rotate in the L5-S1 intervertebral disc 62 space. The shaft 14 can rotate, as shown by arrow 106, about the longitudinal axis of the shaft to further dig the teeth 34 into the tissue.

Figure 15A:
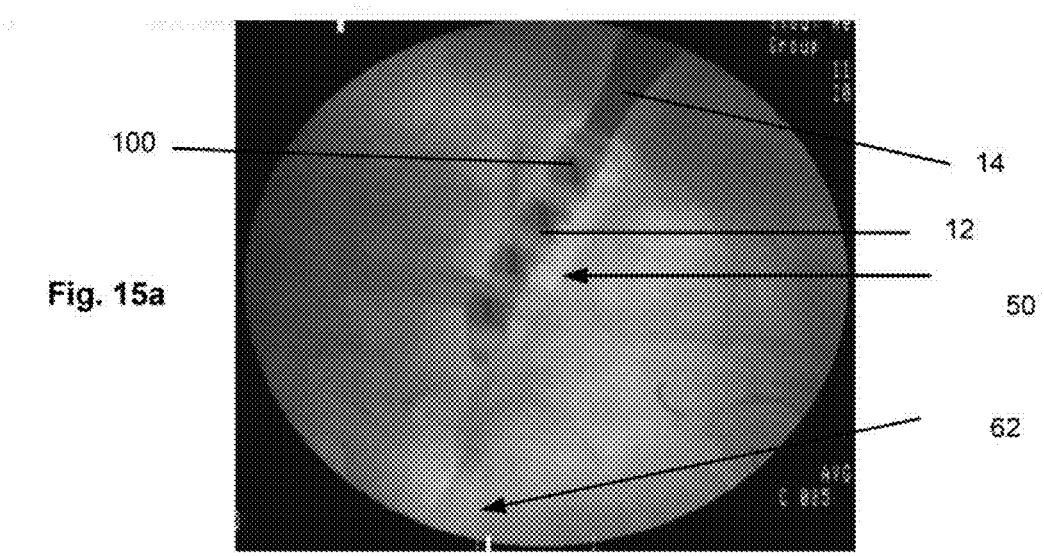
FIGS. 15a through 15c are radiographic visualization of a variation of a method of using the tissue removal device at a target site in the L5-S1 intervertebral space.
Figure 15B:
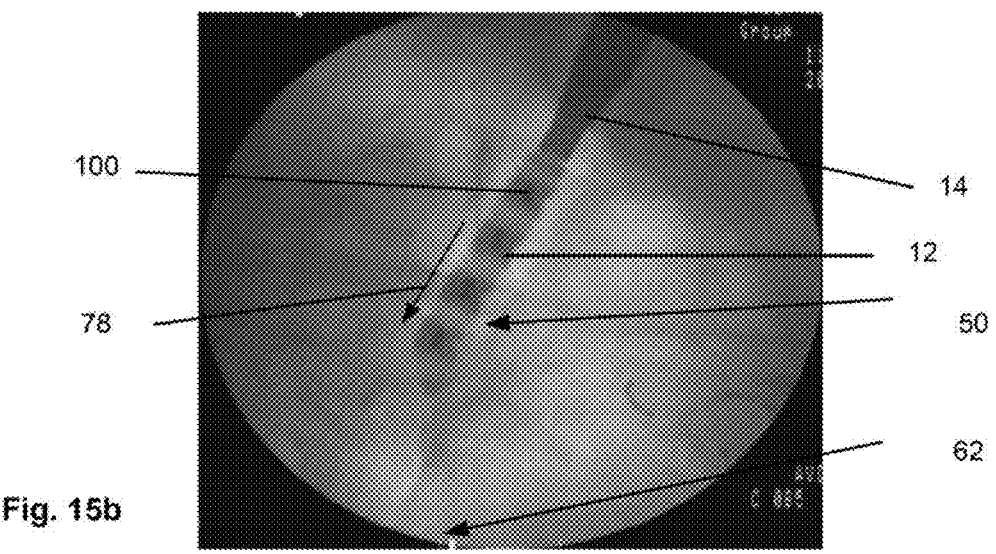
Figure 15C:
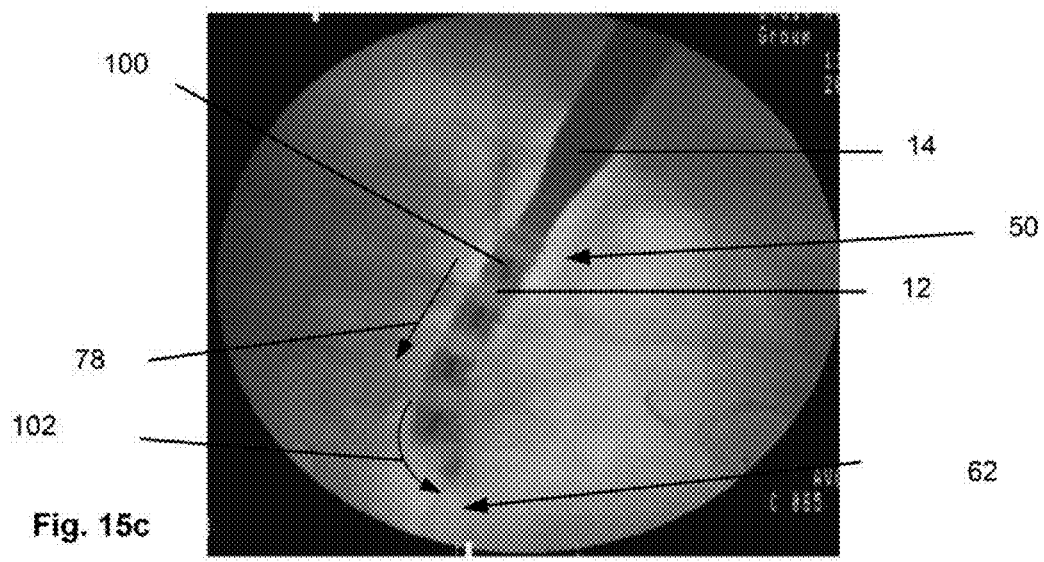

FIGS. 15a through 15c illustrate the delivery of the broach 12 through the transosseous delivery channel 50 and into the L5-S1 intervertebral disc 62. The broach 12 can have one or more radiopaque markers 100, for example one marker 100 in each segment 26.

Any or all elements of the device 10 and/or other devices or apparatuses described herein can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyethylene teraphathalate (PET), polyester (e.g., DACRON® from E. I. Du Pont de Nemours and Company, Wilmington, Del.), poly ester amide (PEA), polypropylene, aromatic polyesters, such as liquid crystal polymers (e.g., Vectran, from Kuraray Co., Ltd., Tokyo, Japan), ultra high molecular weight polyethylene (i.e., extended chain, high-modulus or high-performance polyethylene) fiber and/or yarn (e.g., SPECTRA® Fiber and SPECTRA® Guard, from Honeywell International, Inc., Morris Township, N.J., or DYNEEMA® from Royal DSM N.V., Heerlen, the Netherlands), polytetrafluoroethylene (PTFE), expanded PTFE (ePTFE), polyether ketone (PEK), polyether ether ketone (PEEK), poly ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), poly-L-glycolic acid (PLGA) polylactic acid (PLA), poly-L-lactic acid (PLLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone) any of the other materials listed herein or combinations thereof. Examples of radiopaque materials are barium sulfate, zinc oxide, titanium, stainless steel, nickel-titanium alloys, tantalum and gold.

The device 10 can be made from substantially 100% PEEK, substantially 100% titanium or titanium alloy, or combinations thereof.

Any or all elements of the device and/or other devices or apparatuses described herein, can be, have, and/or be completely or partially coated with agents for cell ingrowth.

The device 10 and/or elements of the device and/or other devices or apparatuses described herein can be filled, coated, layered and/or otherwise made with and/or from cements, tillers, and/or glues known to one having ordinary skill in the art and/or a therapeutic and/or diagnostic agent. Any of these cements and/or fillers and/or glues can be osteogenic and osteoinductive growth factors.

Examples of such cements and/or fillers includes bone chips, demineralized hone matrix (DBM), calcium sulfate, coralline hydroxyapatite, biocoral, tricalcium phosphate, calcium phosphate, polymethyl methacrylate (PMMA), biodegradable ceramics, bioactive glasses, hyaluronic acid, lactoferrin, bone morphogenic proteins (BMPs) such as recombinant human hone morphogenetic proteins (rhBMPs), other materials described herein, or combinations thereof.

The agents within these matrices can include any agent disclosed herein or combinations thereof, including radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor cholene; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; mefenamic acid), COX-2 inhibitors (e.g., VIOXX® from Merck & Co., Inc., Whitehouse Station, N.J.; CELEBREX® from Pharmacia Corp., Peapack, N.J.; COX-1 inhibitors); immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of other agents are provided in Walton et al, Inhibition of Prostoglandin $E_2$ Synthesis in Abdominal Aortic Aneurysms, Circulation, Jul. 6, 1999, 48-54; Tambiah et al, Provocation of Experimental Aortic Inflammation Mediators and Chlamydia Pneumoniae, Brit. J. Surgery 88 (7), 935-940; Franklin et al, Uptake of Tetracycline by Aortic Aneurysm Wall and Its Effect on Inflammation and Proteolysis, Brit. J. Surgery 86 (6), 771-775; Xu et al, Sp1 Increases Expression of Cyclooxygenase-2 in Hypoxic Vascular Endothelium, J. Biological Chemistry 275 (32) 24583-24589; and Pyo et al, Targeted Gene Disruption of Matrix Metalloproteinase-9 (Gelatinase B) Suppresses Development of Experimental Abdominal Aortic Aneurysms, J. Clinical Investigation 105 (11), 1641-1649 which are all incorporated by reference in their entireties.

Any elements described herein as singular can be pluralized (i.e., anything described as "one" can be more than one). Any species element of a genus element can have the characteristics or elements of any other species element of that genus. The above-described configurations, elements or complete assemblies and methods and their elements for carrying out the invention, and variations of aspects of the invention can be combined and modified with each other in any combination.

We claim:

1. A method for removing tissue from a biological target site in a patient comprising:

inserting a multi-segmented articulating broach into the target site, wherein the broach comprises a first segment longitudinally distal to a second segment, and wherein the first segment is rotatably attached to the second segment, and wherein inserting comprises rotating the first segment with respect to the second segment, and wherein the rotation has a component of rotation around an axis parallel with a sagittal axis of the patient.

2. The method of claim 1, further comprising forming a channel through an obstructing bone.

3. The method of claim 2, wherein inserting comprises translating the broach through the channel.

4. The method of claim 3, wherein inserting further comprises articulating the broach while the broach is located at the target site.

5. The method of claim 4, wherein the broach comprises teeth extending across the width of the broach.

6. The method of claim 1, further comprising removing the broach from the target site.

7. The method of claim 1, further comprising capturing tissue debris in the broach.

8. The method of claim 1, further comprising removing the broach from the target site, wherein removing the broach from the target site comprises removing tissue debris from the target site.

9. The method of claim 1, wherein the target site comprises an L5-S1 intervertebral disc space.

10. The method of claim 1, wherein the broach comprises teeth extending across the width of the broach.

11. A method for removing tissue from a biological target site in a patient comprising:
   inserting a multi-segmented articulating broach into the target site, wherein the broach comprises teeth, and wherein inserting comprises articulating between at least two segments of the broach, and wherein the articulation comprises rotating around an axis parallel with a sagittal axis of the patient; and
   debriding the tissue comprising oscillating the broach at the target site, further comprising scraping the tissue with at least some of the teeth.

12. The method of claim 11, further comprising forming a channel through an obstructing bone.

13. The method of claim 12, wherein inserting comprises translating the broach through the channel.

14. The method of claim 13, wherein inserting further comprises articulating the broach while the broach is located at the target site.

15. The method of claim 14, wherein the broach comprises teeth extending across the width of the broach.

16. The method of claim 11, further comprising removing the broach from the target site.

17. The method of claim 11, further comprising capturing tissue debris in the broach.

18. The method of claim 11, further comprising removing the broach from the target site, wherein removing the broach from the target site comprises removing tissue debris from the target site.

19. The method of claim 11, wherein the target site comprises an L5-S1 intervertebral disc space.

20. The method of claim 11, wherein the broach comprises teeth extending across the width of the broach.

* * * * *